US011904092B2

(12) United States Patent
Wada et al.

(10) Patent No.: US 11,904,092 B2
(45) Date of Patent: Feb. 20, 2024

(54) AIR-BLOWING DEVICE AND FLUID CONTROL APPARATUS

(71) Applicant: Murata Manufacturing Co., Ltd., Kyoto (JP)

(72) Inventors: Hiroaki Wada, Kyoto (JP); Atsuhiko Hirata, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1170 days.

(21) Appl. No.: 16/595,600

(22) Filed: Oct. 8, 2019

(65) Prior Publication Data

US 2020/0038606 A1 Feb. 6, 2020

Related U.S. Application Data

(63) Continuation of application No. PCT/JP2018/013826, filed on Mar. 30, 2018.

(30) Foreign Application Priority Data

Apr. 10, 2017 (JP) ................. 2017-077430

(51) Int. Cl.
*A61M 16/00* (2006.01)
*A61M 16/06* (2006.01)
*F04D 29/66* (2006.01)

(52) U.S. Cl.
CPC .... *A61M 16/0066* (2013.01); *A61M 16/0666* (2013.01); *F04D 29/663* (2013.01); *A61M 2205/3365* (2013.01); *A61M 2205/42* (2013.01); *A61M 2205/505* (2013.01)

(58) Field of Classification Search
CPC ..................... A61M 16/0057; A61M 16/0066
See application file for complete search history.

(56) References Cited

U.S. PATENT DOCUMENTS

| 7,328,586 B2 * | 2/2008 | Gau ....................... F24F 13/24 |
| | | 62/158 |
| 9,855,397 B2 * | 1/2018 | Peake ............... A61M 16/0875 |
| 10,201,676 B2 | 2/2019 | Lithgow et al. |
| 2007/0169781 A1 * | 7/2007 | Tang ..................... A61M 16/00 |
| | | 128/205.25 |

(Continued)

FOREIGN PATENT DOCUMENTS

| CN | 2620296 | * | 6/2004 |
| CN | 2620296 Y | | 6/2004 |

(Continued)

OTHER PUBLICATIONS

Office Action for Chinese Patent Application No. 201880024048.2 dated Jan. 7, 2022.

(Continued)

*Primary Examiner* — Michael J Tsai
(74) *Attorney, Agent, or Firm* — Pearne & Gordon LLP

(57) ABSTRACT

An air-blowing device 10A includes an air blower 50 and a housing 20 that includes an intake hole 41a into which a fluid flows as a result of the air blower 50 being driven and an exhaust portion from which the fluid is discharged as a result of the air blower 50 being driven and that accommodates the air blower 50. The housing 20 is capable of expanding and contracting so as to change the internal volume of the housing 20.

20 Claims, 19 Drawing Sheets

(56) References Cited

U.S. PATENT DOCUMENTS

| | | | |
|---|---|---|---|
| 2014/0299130 A1* | 10/2014 | Librett | A61M 16/107 29/428 |
| 2017/0211438 A1 | 7/2017 | Suzuki et al. | |
| 2018/0169359 A1 | 6/2018 | Higashiyama et al. | |

FOREIGN PATENT DOCUMENTS

| | | |
|---|---|---|
| CN | 106456924 A | 2/2017 |
| JP | 2007-092672 A | 4/2007 |
| JP | 2007-239625 A | 9/2007 |
| JP | 2008-518640 A | 6/2008 |
| JP | 2011-117442 A | 6/2011 |
| JP | 2013-040592 A | 2/2013 |
| JP | 2016-034411 A | 3/2016 |
| WO | 2014/147675 A1 | 9/2014 |
| WO | 2017/029950 A1 | 2/2017 |

OTHER PUBLICATIONS

International Search Report for International Application No. PCT/JP2018/013826 dated Jun. 12, 2018.
Written Opinion for International Application No. PCT/JP2018/013826 dated Jun. 12, 2018.
Office action for Japanese patent application 2019-512435 dated Jul. 7, 2020.

\* cited by examiner

FIG. 13
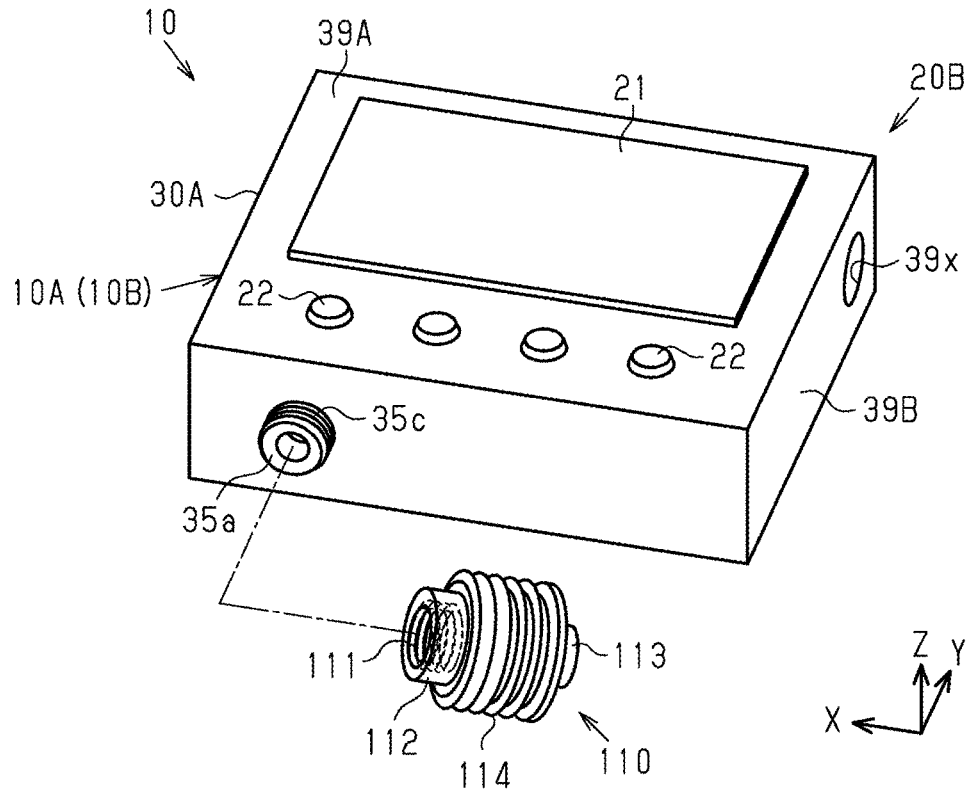
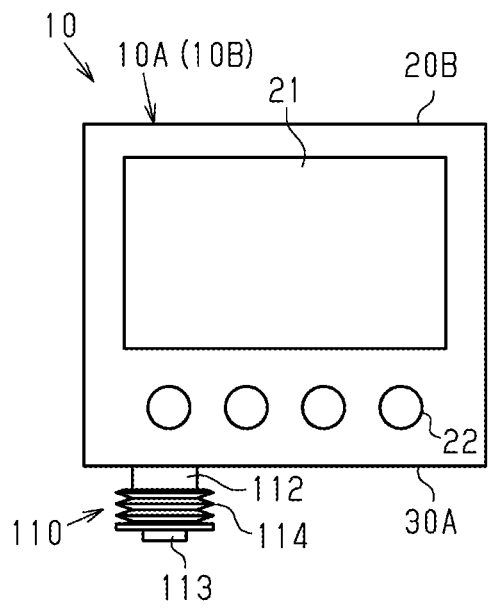
FIG. 14A
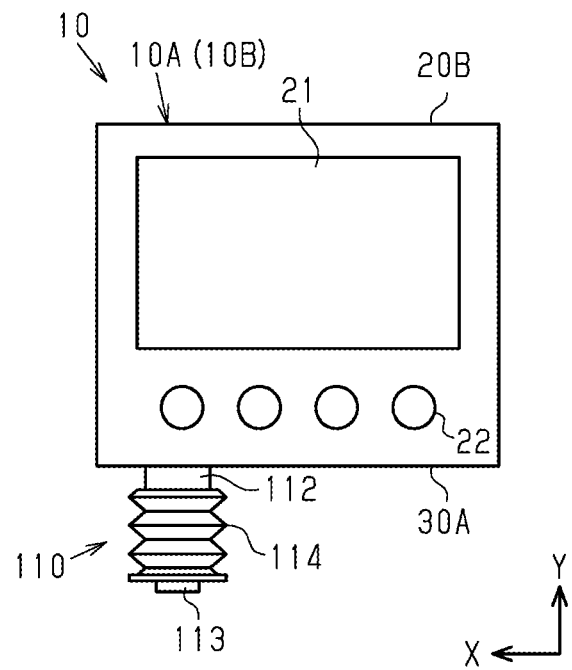
FIG. 14B

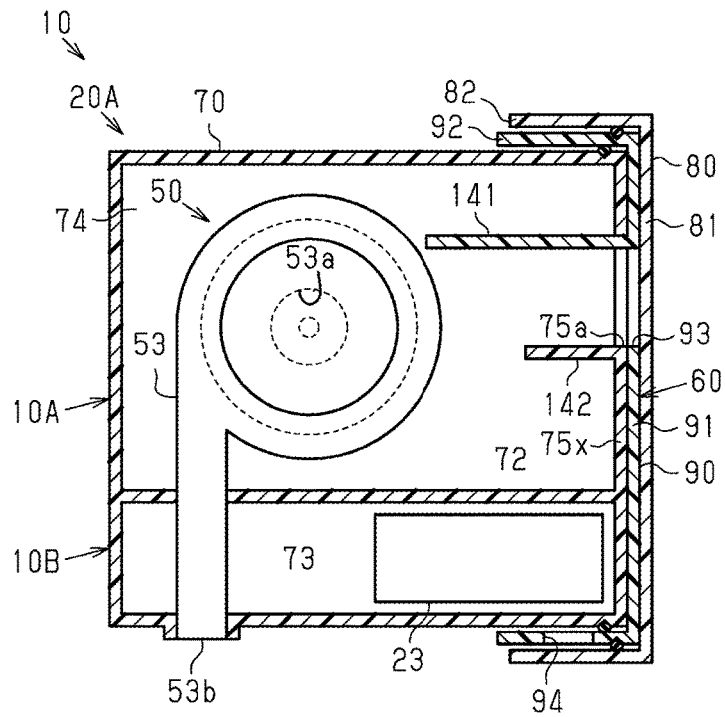
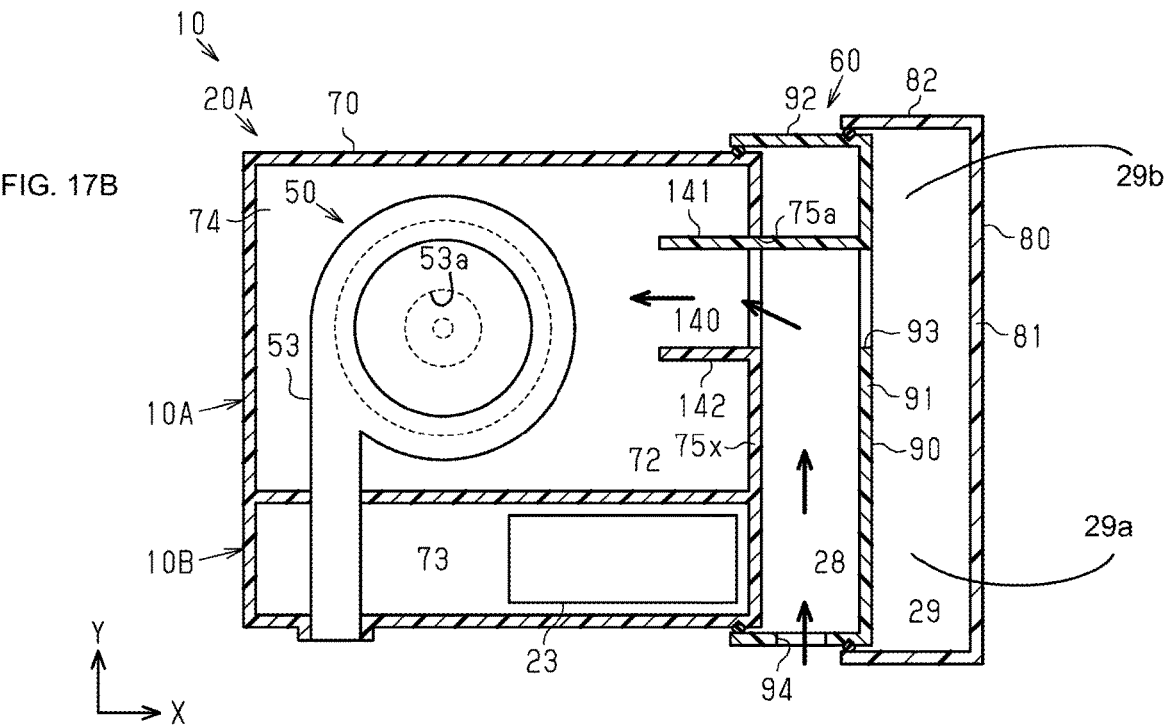

FIG. 19A
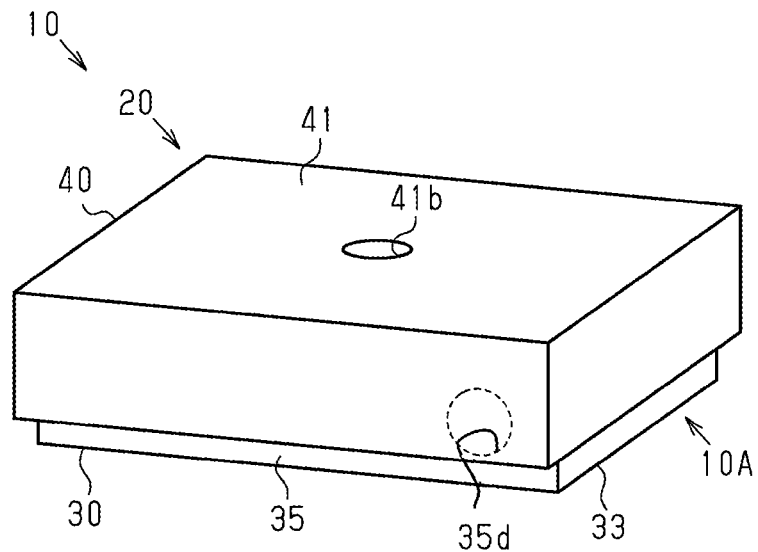
FIG. 19B
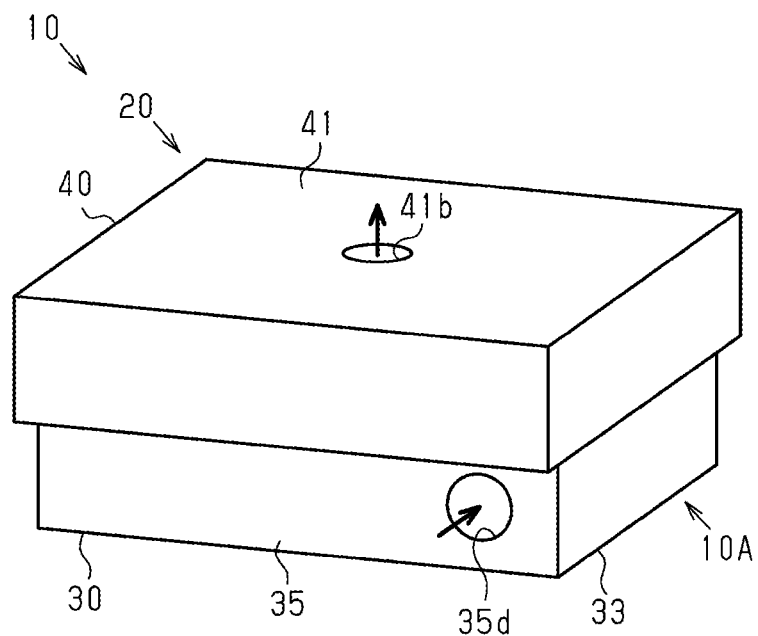
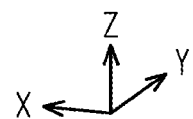

FIG. 22A
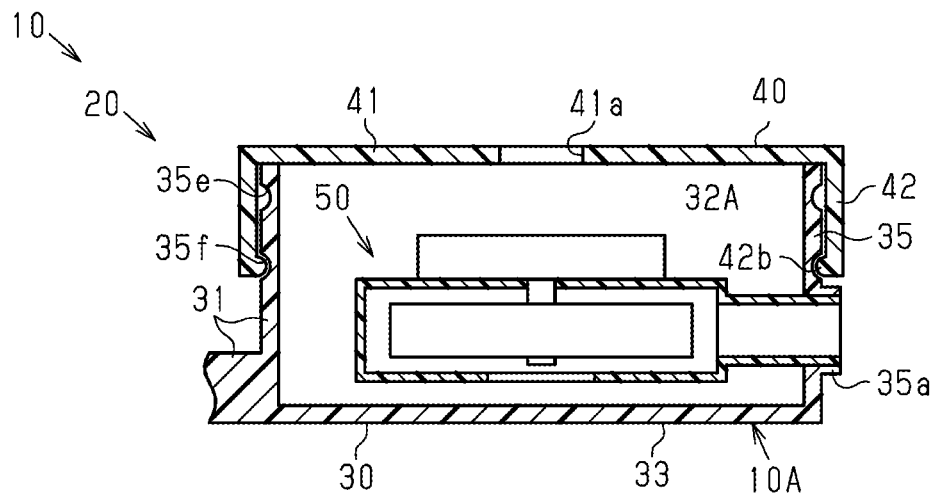
FIG. 22B
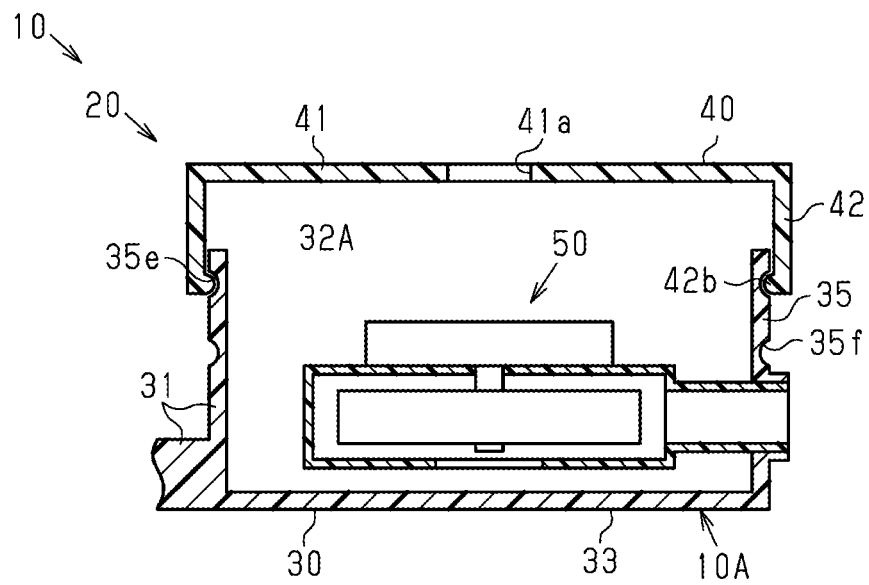
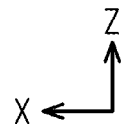

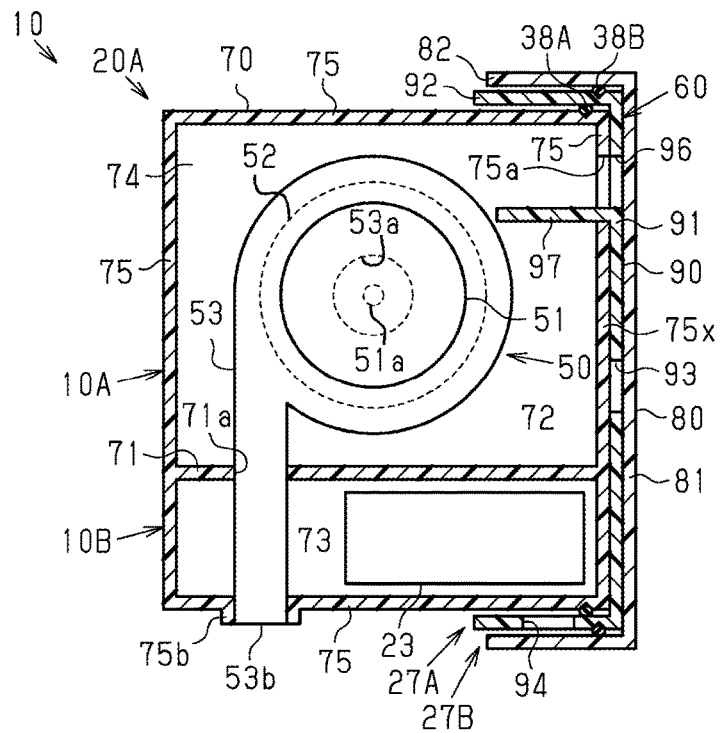
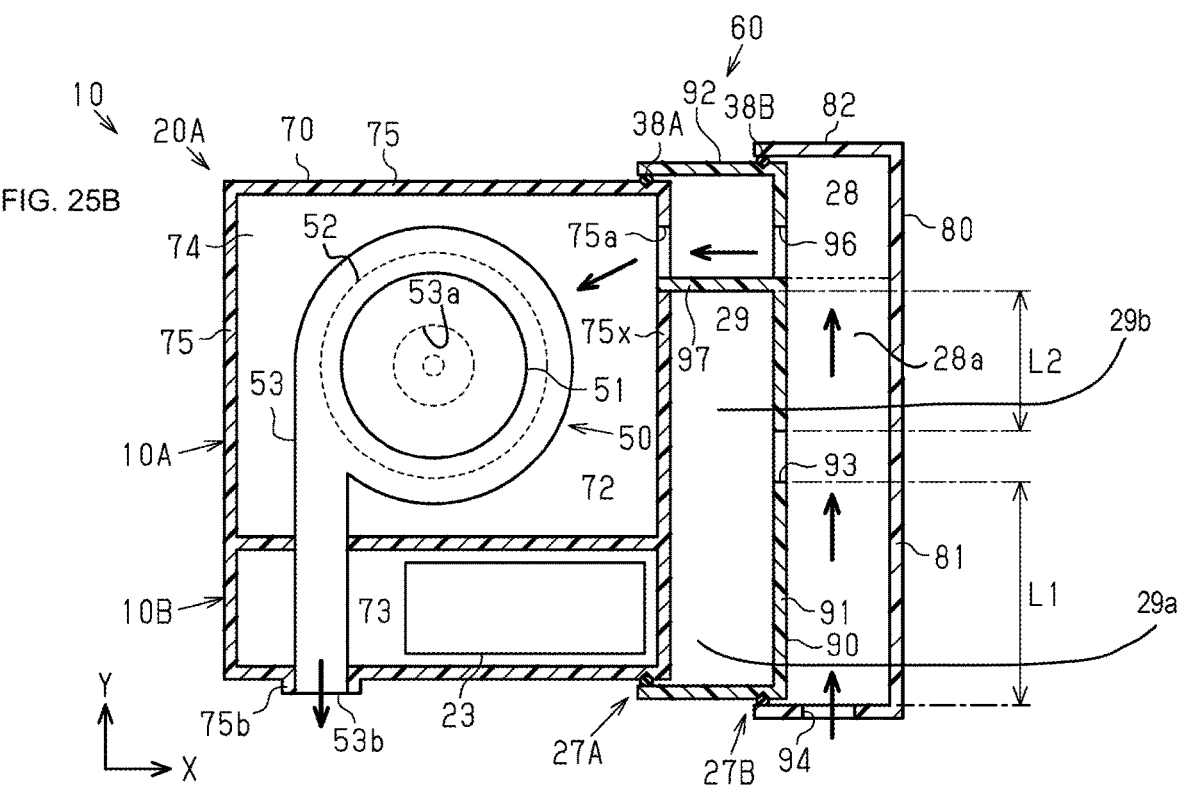
FIG. 25B

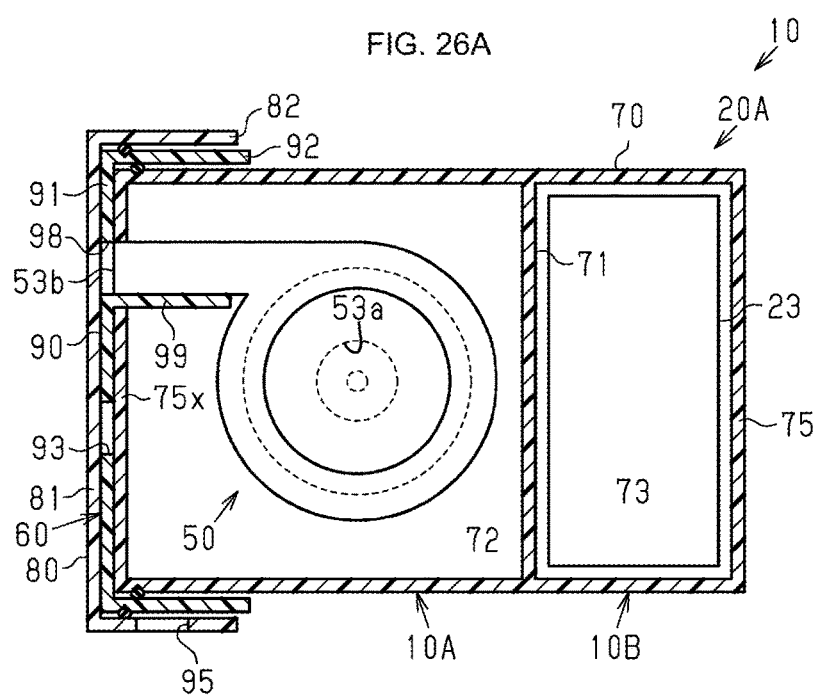
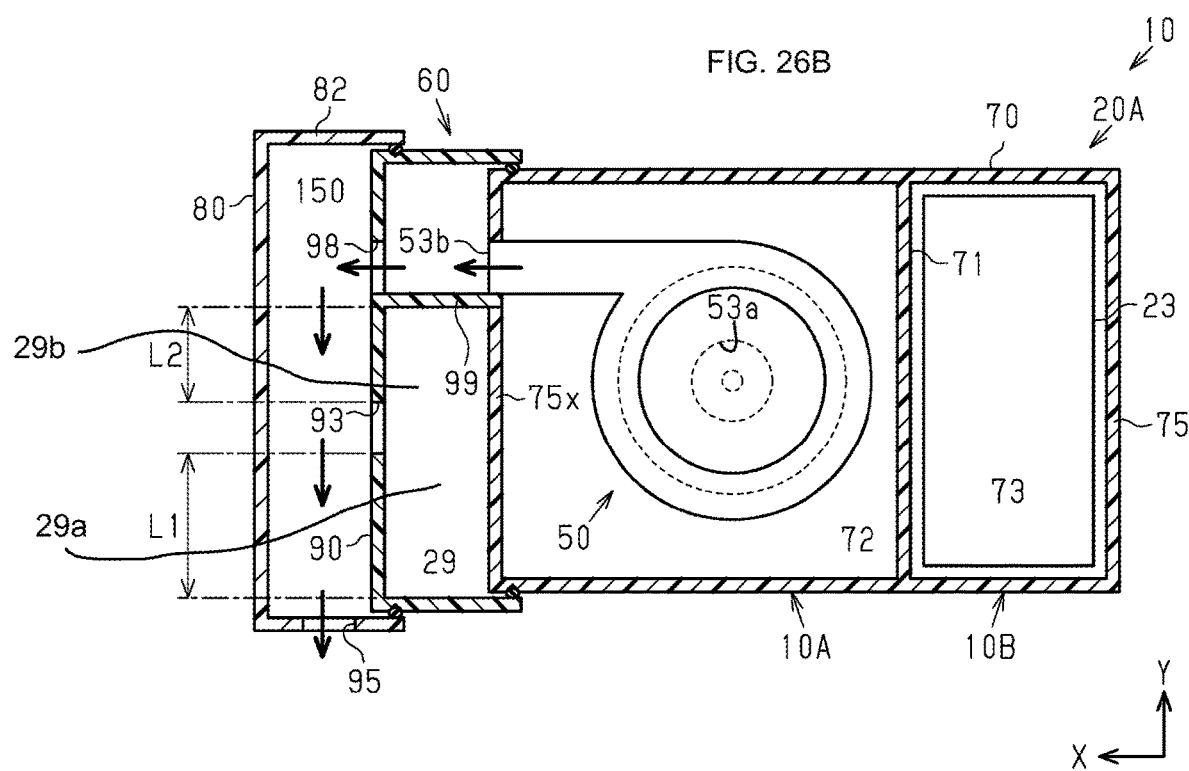

AIR-BLOWING DEVICE AND FLUID CONTROL APPARATUS

This is a continuation of International Application No. PCT/JP2018/013826 filed on Mar. 30, 2018 which claims priority from Japanese Patent Application No. 2017-077430 filed on Apr. 10, 2017. The contents of these applications are incorporated herein by reference in their entireties.

BACKGROUND OF THE DISCLOSURE

Field of the Disclosure

The present disclosure relates to an air-blowing device and a fluid control apparatus that are used for, for example, positive airway pressure (PAP).

Description of the Related Art

In the related art, for example, a fluid control apparatus such as a continuous positive airway pressure (CPAP) apparatus is used for treating sleep-related disorders including obstructive sleep apnea (OSA) syndrome. A fluid control apparatus includes, for example, an apparatus body with a built-in fan and supplies a gas (e.g., air) from the apparatus body to a mask that is attached to the face of a patient at a constant pressure that is higher than atmospheric pressure. Such a fluid control apparatus is driven when a patient sleeps, and thus, quietness is required. Patent Documents 1 and 2 each describe a fluid control apparatus with improved quietness as an example.
Patent Document 1: Japanese Unexamined Patent Application Publication (Translation of PCT Application) No. 2008-518640
Patent Document 2: Japanese Unexamined Patent Application Publication No. 2016-34411

BRIEF SUMMARY OF THE DISCLOSURE

The quietness of a fluid control apparatus is improved as the volume of a silencer cavity increases, and on the other hand, the size of the fluid control apparatus increases. Thus, for example, when the fluid control apparatus is carried by a patient as the patient goes out, the portability of the fluid control apparatus is low.

It is an object of the present disclosure to provide an air-blowing device and a fluid control apparatus capable of improving the portability thereof when not in use.

An air-blowing device according to an aspect of the present disclosure that solves the above-described problem includes an air blower and a housing that includes a first cavity into which a fluid flows as a result of the air blower being driven and a second cavity from which the fluid is discharged as a result of the air blower being driven and that accommodates the air blower. The housing is capable of expanding and contracting so as to change an internal volume of the housing.

With this configuration, when the air blower is driven, the housing is expanded, so that the internal volume of the housing increases, and as a result, a decrease in the quietness of the air-blowing device can be suppressed. In addition, when the air blower is not driven, that is, for example, when a patient carries the air-blowing device, the housing is contracted, so that the internal volume of the housing is reduced. As a result, the housing becomes small in size. Thus, the portability of the air-blowing device when the air-blowing device is not in use can be improved.

In the above-described air-blowing device according to the aspect of the present disclosure, the housing includes a first portion in which the air blower is disposed and a second portion that covers a direction of the first portion, and the housing is capable of expanding and contracting so as to change a volume of an internal space that is surrounded by the first portion and the second portion.

With this configuration, when the air blower is driven, the volume of the internal space surrounded by the first portion and the second portion is increased, so that a silencing effect corresponding to the amount by which the volume of the internal space increases can be obtained, and thus, a decrease in the quietness of the air-blowing device can be suppressed. In addition, when the air blower is not driven, that is, for example, when a patient carries the air-blowing device, the volume of the internal space surrounded by the first portion and the second portion is reduced, so that the housing becomes small in size. Therefore, the portability of the air-blowing device when the air-blowing device is not in use can be improved.

In the above-described air-blowing device according to the aspect of the present disclosure, the housing includes a movable unit that causes the first portion and the second portion to move relative to each other.

With this configuration, the movable unit can cause the first portion and the second portion to move relative to each other, and thus, the volume of the internal space surrounded by the first portion and the second portion can be easily changed.

In the above-described air-blowing device according to the aspect of the present disclosure, the housing includes a partition-wall portion by which a space inside the first portion and a space inside the second portion are partitioned from each other, and the partition-wall portion has a communication portion that allows the communication between the space inside the first portion and the space inside the second portion.

With this configuration, the space surrounded by the first portion and the partition-wall portion and the space surrounded by the second portion and the partition-wall portion are partitioned from each other by the partition-wall portion. As a result, the space surrounded by the second portion and the partition-wall portion becomes a space dedicated to a silencer, and thus, the silencing effect is improved.

In the above-described air-blowing device according to the aspect of the present disclosure, the second portion includes the first cavity or the second cavity, and an opening surface of the communication portion, the opening surface being located on the second portion side, faces an opening surface of the first cavity or the second cavity, which is included in the second portion.

With this configuration, the behavior of acoustic waves in a second space and the behavior of their reflected waves are more predictable than those in a configuration in which the opening surface of the first cavity and the opening surface of the communication portion that is located on the second portion side do not face each other, and thus, it is easier to create the characteristics of a silencer in the second space.

The above-described air-blowing device according to the aspect of the present disclosure further includes a suction path that allows the communication between the first cavity and a suction port of the air blower. The partition-wall portion includes a first partition-wall portion and a second partition-wall portion. The first partition-wall portion is disposed between the first portion and the second partition-wall portion. The second partition-wall portion is disposed between the first partition-wall portion and the second portion. The first portion includes the second cavity. The suction path is formed between the first partition-wall portion and the second partition-wall portion or between the second partition-wall portion and the second portion.

With this configuration, in the case where the suction path is formed between the first partition-wall portion and the second partition-wall portion, the space surrounded by the second partition-wall portion and the second portion is formed outside the first portion and becomes a space dedicated to a silencer. As a result, the silencing effect is improved. In addition, in the case where the suction path is formed between the second partition-wall portion and the second portion, the space surrounded by the first partition-wall portion and the second partition-wall portion is formed outside the first portion and becomes a space dedicated to a silencer. As a result, the silencing effect is improved.

The above-described air-blowing device according to the aspect of the present disclosure further includes a discharge path that allows the communication between the second cavity and a discharge port of the air blower. The partition-wall portion includes a first partition-wall portion and a second partition-wall portion. The first partition-wall portion is disposed between the first portion and the second partition-wall portion. The second partition-wall portion is disposed between the first partition-wall portion and the second portion. The first portion includes the first cavity. The discharge path is formed between the first partition-wall portion and the second partition-wall portion or between the second partition-wall portion and the second portion.

With this configuration, in the case where the discharge path is formed between the first partition-wall portion and the second partition-wall portion, the space surrounded by the second partition-wall portion and the second portion is formed outside the first portion and becomes a space dedicated to a silencer. As a result, the silencing effect is improved. In addition, in the case where the discharge path is formed between the second partition-wall portion and the second portion, the space surrounded by the first partition-wall portion and the second partition-wall portion is formed outside the first portion and becomes a space dedicated to a silencer. As a result, the silencing effect is improved.

In the above-described air-blowing device according to the aspect of the present disclosure, the second partition-wall portion is attached to the first portion so as to be movable relative to the first portion.

With this configuration, the volume of the suction path or the discharge path can be changed, and thus, when the air blower is not driven, that is, for example, when a patient carries the air-blowing device, the volume of the suction path or the discharge path is reduced, so that the housing becomes small in size. Therefore, the portability of the air-blowing device can be improved.

In the above-described air-blowing device according to the aspect of the present disclosure, the second portion is attached to the second partition-wall portion so as to be movable relative to the second partition-wall portion, and a direction of movement of the second partition-wall portion with respect to the first portion and a direction of movement of the second portion with respect to the second partition-wall portion are the same direction.

With this configuration, as a result of a patient moving the second partition-wall portion and the second portion in one predetermined direction, the space surrounded by the first partition-wall portion and the second partition-wall portion and the space surrounded by the second partition-wall portion and the second portion are formed. Thus, an operation for forming the space surrounded by the first partition-wall portion and the second partition-wall portion and the space surrounded by the second partition-wall portion and the second portion, that is, an operation for forming the suction path or the discharge path or a space dedicated to a silencer can be easily performed by the patient.

In the above-described air-blowing device according to the aspect of the present disclosure, the second portion includes a partition unit that partitions an internal space formed of the second partition-wall portion and the second portion.

With this configuration, the space (the space surrounded by the second partition-wall portion and the second portion or the space surrounded by the first partition-wall portion and the second partition-wall portion) that communicates with the suction path or the discharge path via the communication portion is caused to extend from the communication portion in only one direction by the partition unit. Thus, in the case where the suction path or the discharge path is formed between the first partition-wall portion and the second partition-wall portion, the acoustic waves that enters the communication portion, propagates through the space surrounded by the second partition-wall portion and the second portion, and is reflected so as to return to the communication portion effectively cancel out acoustic waves of a specific frequency in the suction path or the discharge path. In addition, in the case where the suction path or the discharge path is formed between the second partition-wall portion and the second portion, the acoustic waves that enters the communication portion, propagates through the space surrounded by the first partition-wall portion and the second partition-wall portion, and is reflected so as to return to the communication portion effectively cancel out acoustic waves of a specific frequency in the suction path or the discharge path.

In the above-described air-blowing device according to the aspect of the present disclosure, the movable unit connects the first portion and the second portion to each other so as to be capable of hermetically sealing an internal space between the first portion and the second portion and is capable of expanding and contracting in a direction in which the first portion and the second portion move relative to each other.

With this configuration, the probability of the air leaking from a gap between the first portion and the second portion to the outside of the housing can be reduced. Thus, a decrease in the flow-rate characteristics of the air-blowing device can be suppressed.

In the above-described air-blowing device according to the aspect of the present disclosure, the movable unit is capable of causing the first portion and the second portion to move relative to each other between a first form in which one of the first portion and the second portion is accommodated in another one of the first portion and the second portion and a second form in which the one of the first portion and the second portion, which has been accommodated, projects from the other one of the first portion and the second portion.

With this configuration, in the first form in which the volume of the internal space between the first portion and the second portion is reduced, one of the first portion and the second portion is accommodated in another one of the first portion and the second portion, and thus, the reduction in the size of the housing in the first form is further facilitated compared with a configuration in which one of the first portion and the second portion is not accommodated in the other of the first portion and the second portion.

In the above-described air-blowing device according to the aspect of the present disclosure, the housing further includes a silencer that is detachably attached to the first cavity or the second cavity, and the silencer is capable of expanding and contracting so as to change an internal volume of the silencer.

With this configuration, when the air blower is not driven, that is, for example, when a patient carries the air-blowing device, the volume of the housing is reduced by contracting the silencer, so that the size of the housing is reduced. Therefore, the portability of the air-blowing device when the air-blowing device is not in use can be improved.

In the above-described air-blowing device according to the aspect of the present disclosure, a rotational speed of the air blower is settable to any one of a plurality of speed levels, and the housing is capable of changing the internal volume of the housing to any one of a plurality of volume levels.

With this configuration, by changing the internal volume of the housing, the frequency at which the transmission loss based on the rotational speed of the air blower becomes zero can be avoided. Therefore, a decrease in the quietness of the air-blowing device when in use can be suppressed.

A fluid control apparatus according to another aspect of the present disclosure that solves the above-described problem includes the above-described air-blowing device and a tube that connects the second cavity of the air-blowing device to a mask or a nasal cannula and supplies a gas from the second cavity to the mask or the nasal cannula.

With this configuration, as in the above-described air-blowing device, a decrease in the quietness of the fluid control apparatus when in use can be suppressed, and the portability of the fluid control apparatus when not in use can be improved.

According to the air-blowing device and the fluid control apparatus of the present disclosure, the portability of the air-blowing device and the fluid control apparatus when not in use can be improved.

BRIEF DESCRIPTION OF THE SEVERAL VIEWS OF THE DRAWINGS

FIG. 13 is an exploded perspective view of an air-blowing device and a silencer in a fluid control apparatus according to a fifth embodiment.

FIG. 14A is a plan view of the air-blowing device when the air-blowing device is in the first form, and FIG. 14B is a plan view of the air-blowing device when the air-blowing device is in the second form.

FIG. 17A is a plan sectional view of an air-blowing device in a fluid control apparatus according to another modification when the air-blowing device is in the first form, and FIG. 17B is a plan sectional view of the air-blowing device in the fluid control apparatus according to this modification when the air-blowing device is in the second form.

FIG. 19A is a perspective view of an air-blowing device in a fluid control apparatus according to another modification when the air-blowing device is in the first form, and FIG. 19B is a perspective view of the air-blowing device in the fluid control apparatus according to this modification when the air-blowing device is in the second form.

FIG. 22A is a sectional side view of an air-blowing device in a fluid control apparatus according to another modification when the air-blowing device is in the first form, and FIG. 22B is a sectional side view of the air-blowing device in the fluid control apparatus according to this modification when the air-blowing device is in the second form.

FIG. 25A is a plan sectional view of an air-blowing device in a fluid control apparatus according to another modification when the air-blowing device is in the first form, and FIG. 25B is a plan sectional view of the air-blowing device in the fluid control apparatus according to this modification when the air-blowing device is in the second form.

FIG. 26A is a plan sectional view of an air-blowing device in a fluid control apparatus according to another modification when the air-blowing device is in the first form, and FIG. 26B is a plan sectional view of the air-blowing device in the fluid control apparatus according to this modification when the air-blowing device is in the second form.

DETAILED DESCRIPTION OF THE DISCLOSURE

Figure 1:
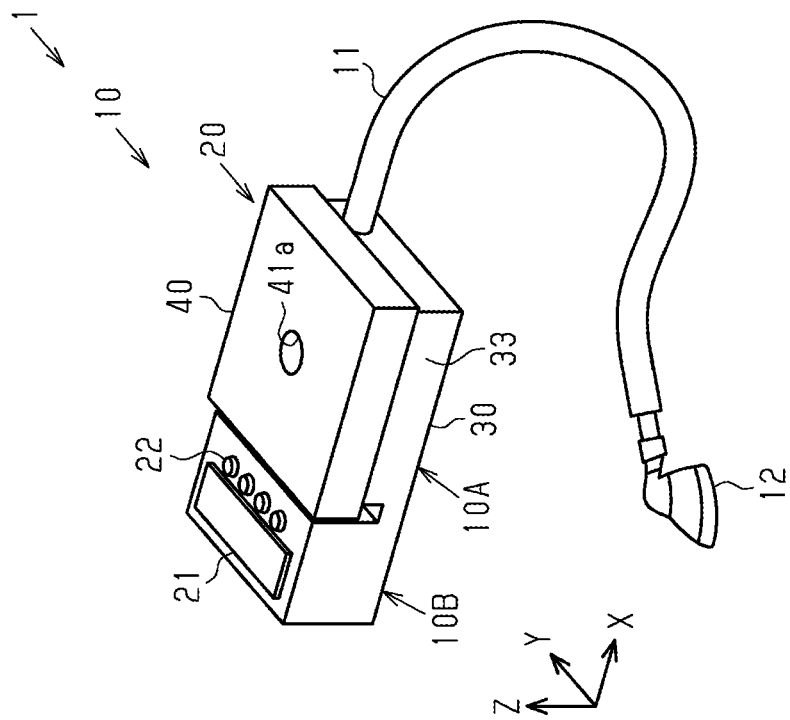
FIG. 1 a perspective view of a fluid control apparatus according to a first embodiment of the present disclosure in which an air-blowing device is in a first form.

Embodiments of an air-blowing device and a fluid control apparatus that includes the air-blowing device will be described with reference to the drawings.

Note that some components may sometimes be illustrated in an enlarged manner in the accompanying drawings for ease of understanding. The dimensional ratios of the components may sometimes be different from the dimensional ratios of actual components or may sometimes differ between those in the drawings. In addition, the hatching for some of the components is omitted in the cross-sectional views for ease of understanding.

First Embodiment

Figure 2:
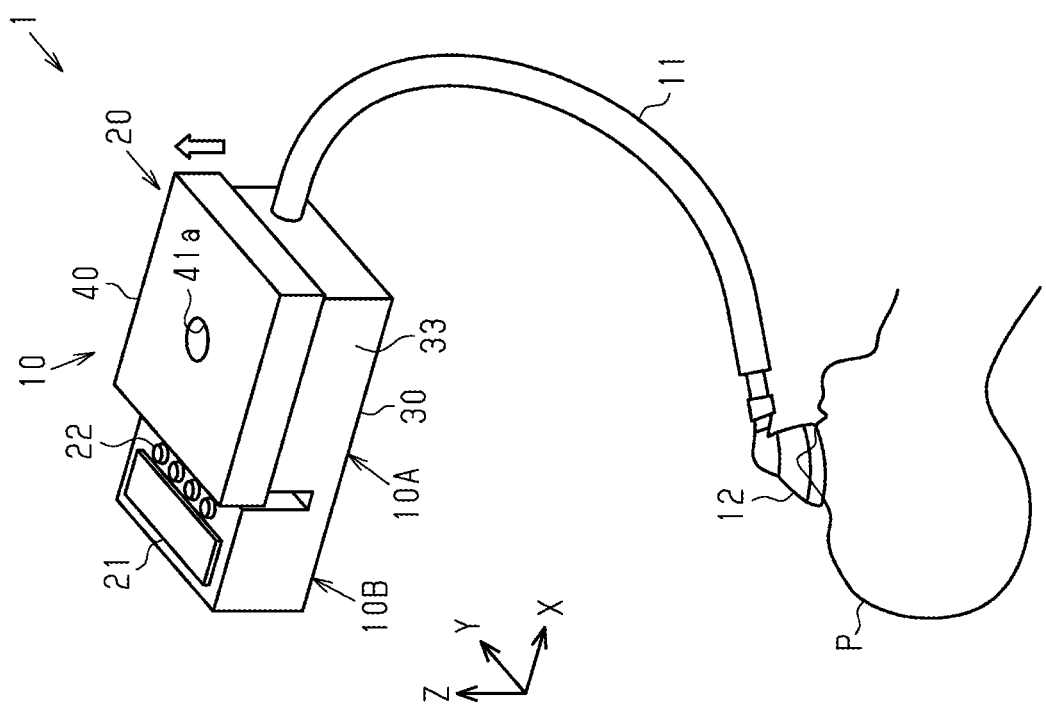
FIG. 2 a perspective view of the fluid control apparatus according to the first embodiment in which the air-blowing device is in a second form.

As illustrated in FIG. 1 and FIG. 2, a fluid control apparatus 1 is used as, for example, a positive airway pressure (PAP) apparatus. The fluid control apparatus 1 includes an apparatus body 10, a tube 11, and a mask 12. The apparatus body 10 includes an air-blowing device 10A that supplies a fluid (e.g., air) to the tube 11 and a control device 10B that controls the air-blowing device 10A. FIG. 1 illustrates a form of the air-blowing device 10A when not in use, that is, for example, the form of the air-blowing device 10A that is carried by a user when the user goes out (hereinafter referred to as a "first form"). FIG. 2 illustrates another form of the air-blowing device 10A when in use (hereinafter referred to as a "second form"). As seen from FIG. 1 and FIG. 2, the air-blowing device 10A in the first form is larger in size than the air-blowing device 10A in the second form. As illustrated in FIG. 2, the air-blowing device 10A is connected to the mask 12 via the tube 11. The mask 12 is attached to the face of a patient P. In the fluid control apparatus 1, the air-blowing device 10A supplies a desired positive pressure fluid (e.g., air) to the nose of the patient P through the tube 11 and the mask 12. As a result, soft tissue around the tongue root of the patient P is expanded, and this suppresses the occurrence of airway narrowing when the patient P breathes.

The fluid control apparatus 1 determines the state of the patient P (e.g., an exhaling state) and controls the pressure of the gas that is to be supplied to the patient P in accordance with the state of the patient P. The fluid control apparatus 1 estimates the timing at which the patient P, to which the mask 12 is attached, exhales. Then, the fluid control apparatus 1 controls the pressure value of the gas, which is to be supplied, at the estimated exhalation timing. For example, the fluid control apparatus 1 supplies the gas at a reference pressure value. For example, the reference pressure value is a pressure value at the time of inhaling, the pressure value being specified by a doctor, and is, for example, 1,000 Pa. Then, the fluid control apparatus 1 changes, at the estimated exhalation timing, the pressure of the gas, which is to be supplied, to a pressure value at the time of exhaling. The pressure value at the time of exhaling is, for example, 700 Pa. In other words, the fluid control apparatus 1 performs control in accordance with the state of the patient P (exhalation or inhalation) such that the pressure of the gas, which is to be supplied, alternates between the reference pressure value and the pressure value at the time of exhaling. When the patient P is in the exhaling state, the pressure of the gas that is supplied is reduced, and this relieves difficulty in breathing that is felt by the patient P.

The apparatus body 10 (the air-blowing device 10A) includes a housing 20. The housing 20 has a rectangular box shape whose longitudinal direction is parallel to a transverse direction X. The housing 20 includes a main body 30. The main body 30 includes a first portion 33 that is included in the air-blowing device 10A. The housing 20 includes a second portion 40 that is fitted onto the first portion 33. The first portion 33 and the second portion 40 are movable relative to each other in a heightwise direction Z of the air-blowing device 10A. The main body 30 (the first portion 33) and the second portion 40 are made of, for example, a resin material. In addition, the air-blowing device 10A includes a display unit 21 and an operation unit 22 that are arranged on a top surface of the main body 30 that is included in the control device 10B. An example of the display unit 21 is a liquid crystal panel. An example of the operation unit 22 is a push button. The control device 10B causes the display unit 21 to display various information items including set values. In addition, the control device 10B sets the various information items including the set values on the basis of an operation performed on the operation unit 22.

Figure 3A:
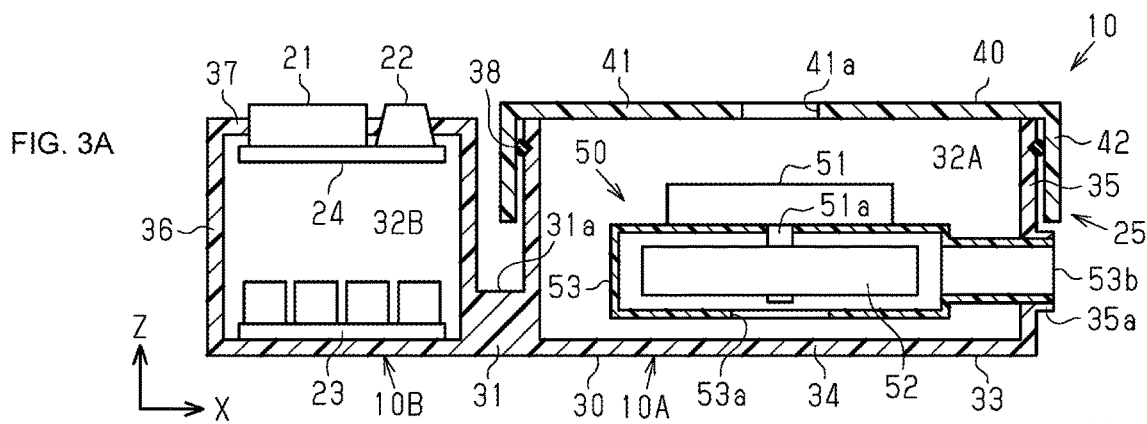
FIG. 3A is a sectional side view of the air-blowing device when the air-blowing device is in the first form.
Figure 3B:
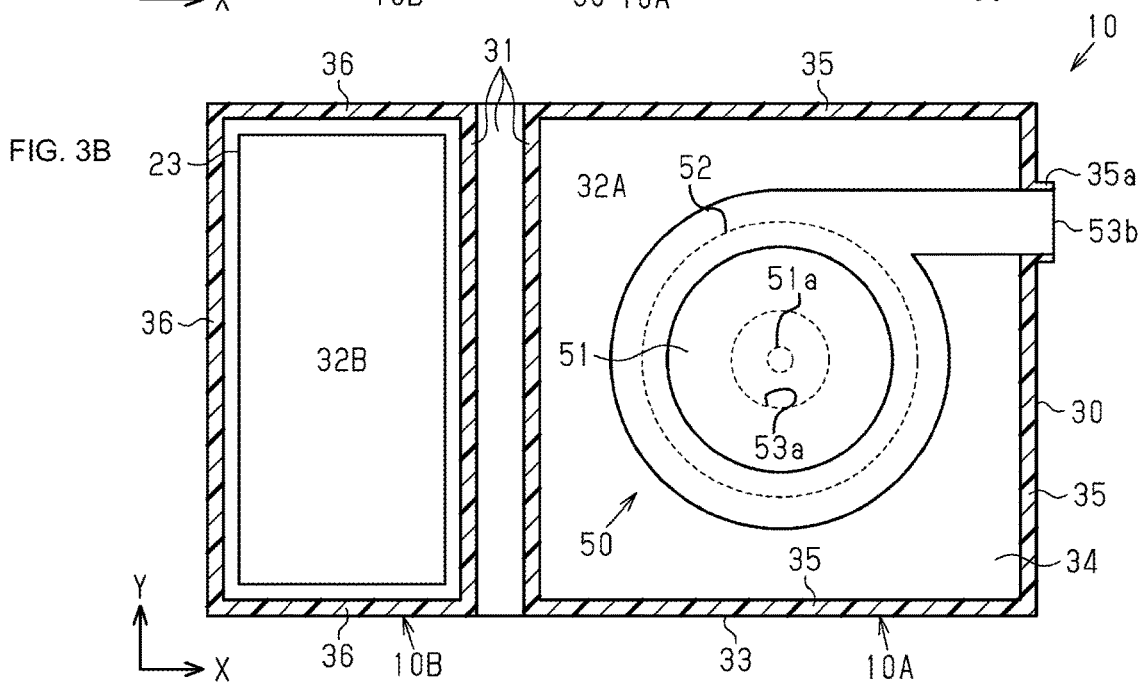
FIG. 3B is a plan sectional view of the air-blowing device.

As illustrated in FIG. 3A and FIG. 3B, the air-blowing device 10A includes an air blower 50. The control device 10B includes a first control circuit board 23 and a second control circuit board 24. The first control circuit board 23 is connected to the air blower 50 and the second control circuit board 24 by an electrical connection member such as a harness (not illustrated). The first control circuit board 23 controls the air blower 50 and the display unit 21 on the basis of an operation performed on the operation unit 22. The display unit 21 and the operation unit 22 are mounted on the second control circuit board 24. The air blower 50 supplies a fluid such as air to the tube 11 (see FIG. 1). An example of the air blower 50 is a centrifugal fan. Note that the configuration of the air blower 50 may be arbitrarily changed. For example, an axial fan may be used as the air blower 50 instead of a centrifugal fan, or a blower may be used as the air blower 50 instead of a fan.

As illustrated in FIG. 3A and FIG. 3B, the interior of the main body 30 is partitioned by a partition wall 31 into an air-blowing chamber 32A and a control chamber 32B. The air-blowing chamber 32A is a space that is surrounded by a bottom surface 34 of the first portion 33, a first side wall 35, and the partition wall 31 so as to be open upward. The control chamber 32B is an enclosed space that is surrounded by the bottom surface 34, which is included in the control device 10B of the main body 30, a second side wall 36, the partition wall 31, and a top wall 37. The air blower 50 is disposed in the air-blowing chamber 32A. The control circuit boards 23 and 24 are disposed in the control chamber 32B. The first side wall 35 extends from the outer peripheral edge of the bottom surface 34, which is included in the air-blowing device 10A, in a direction away from the bottom surface 34 and is connected to the partition wall 31. An exhaust portion 35a that is an example of a second cavity through which the air is discharged from the air blower 50 is formed in a portion of the first side wall 35, the portion facing the partition wall 31 in the transverse direction X. The exhaust portion 35a has a cylindrical shape projecting from the first side wall 35 in the transverse direction X, and the tube 11 (see FIG. 1) is attached to the exhaust portion 35a. The second side wall 36 extends from the outer peripheral edge of the bottom surface 34, which is included in the control device 10B, in a direction away from the bottom surface 34 and is connected to the partition wall 31. The top wall 37 opposes the bottom surface 34, which is included in the control device 10B. The display unit 21 and the operation unit 22 are attached to the top wall 37. As illustrated in FIG. 3A, the partition wall 31 has a recess 31a that is open upward.

The first control circuit board 23 is attached to the bottom surface 34, which is included in the control device 10B. The second control circuit board 24 is attached to the bottom surface of the top wall 37.

The air blower 50 includes a motor 51 that serves as a driving source, an impeller 52 that is mounted on an output shaft 51a of the motor 51, and a case 53 that accommodates the impeller 52. A suction port 53a of the case 53 faces the bottom surface 34 with a gap formed therebetween. A discharge port 53b of the case 53 is connected to the exhaust portion 35a.

The second portion 40 is fitted to the first portion 33 so as to cover the upper opening of the air-blowing chamber 32A. The second portion 40 includes a top wall 41 that faces the bottom surface 34, which is included in the air-blowing device 10A, and a side wall 42 that extends downward from the outer peripheral edge of the top wall 41. An intake hole 41a that is an example of a first cavity is formed in the top wall 41. The side wall 42 is formed along the whole outer peripheral edge of the top wall 41. The side wall 42 that covers partition wall 31 is disposed in the recess 31a.

As illustrated in FIG. 3A, the partition wall 31 and the first side wall 35 of the first portion 33 each face the side wall 42 of the second portion 40 with a gap formed therebetween. The partition wall 31, the first side wall 35, and the side wall 42 form a movable unit 25 that enables the first portion 33 and the second portion 40 to move relative to each other in the heightwise direction Z. The movable unit 25 has a sliding structure.

Figure 3C:
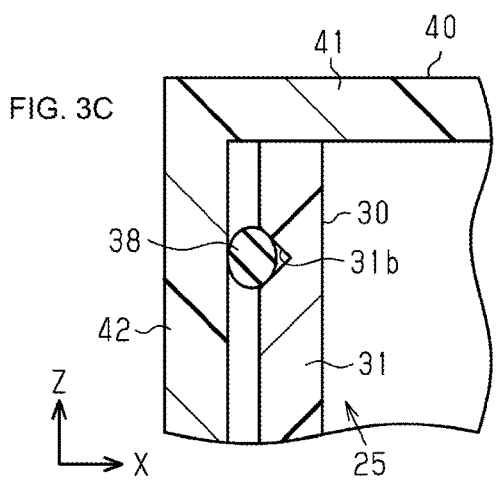
FIG. 3C is an enlarged view of a portion illustrated in FIG. 3A.
Figure 3D:
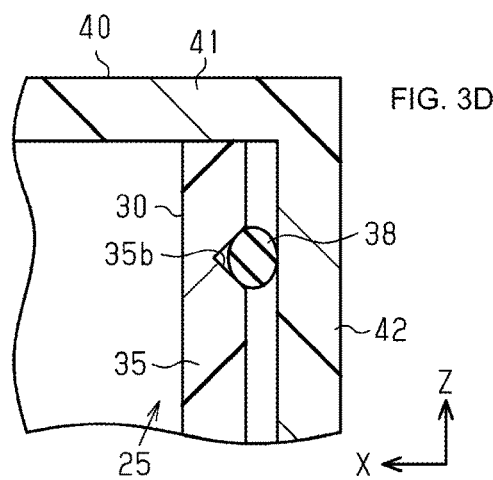
FIG. 3D is an enlarged view of a portion illustrated in FIG. 3A.

An elastic member 38 that is used for hermetically sealing the air-blowing chamber 32A is disposed between the partition wall 31, the first side wall 35, and the side wall 42. An example of the elastic member 38 is an O-ring. As illustrated in FIG. 3C and FIG. 3D, the elastic member 38 is accommodated in a mounting recess 31b of the partition wall 31 and a mounting recess 35b of the first side wall 35. The mounting recess 31b and the mounting recess 35b are continuous with each other. The elastic member 38 is compressed by the first portion 33 and the second portion 40. Grease is applied to a surface of the side wall 42 that faces the partition wall 31 and the first side wall 35.

Forms of the air-blowing device 10A will now be described with reference to FIGS. 3A, 3B, 3C and 3D, and FIG. 4.

Figure 4:
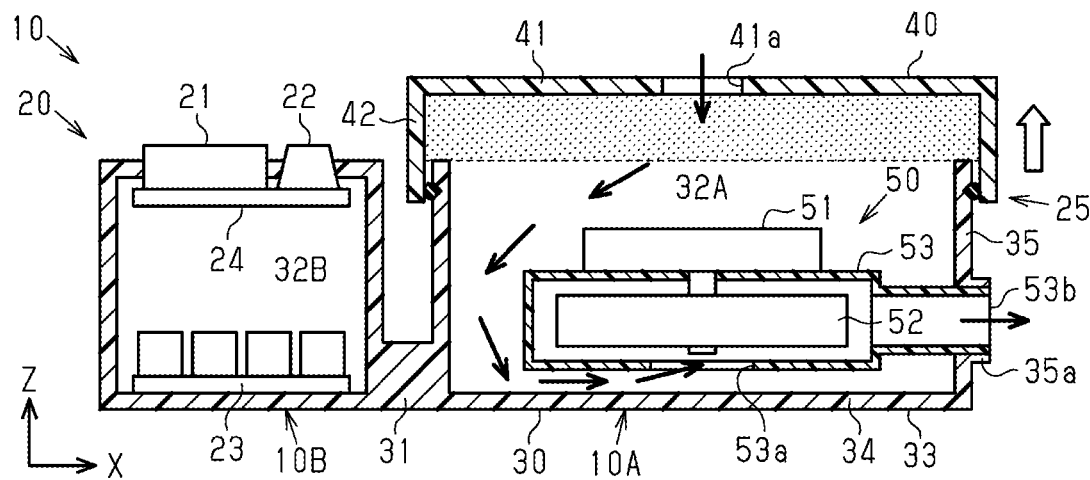
FIG. 4 is a sectional side view of the air-blowing device when the air-blowing device is in the second form.

The form of the air-blowing device 10A can be changed between the first form, which is illustrated in FIG. 3A, and the second form, which is illustrated in FIG. 4, as a result of the patient P (see FIG. 1) manually moving the first portion 33 and the second portion 40 relative to each other.

In the first form of the air-blowing device 10A illustrated in FIG. 3A, the second portion 40 is close to the bottom surface 34 of the first portion 33. More specifically, the bottom surface 34 of the first portion 33 and the top wall 41 of the second portion 40 are closest to each other within a relative movement range of the first portion 33 and the second portion 40 in the heightwise direction Z. In other words, in the first form of the air-blowing device 10A, the volume of the air-blowing chamber 32A that is an enclosed space surrounded by the first portion 33 and the second portion 40 is smallest. As illustrated in FIG. 3A, the partition wall 31 and the first side wall 35 of the first portion 33 are accommodated in a space surrounded by the top wall 41 and the side wall 42 of the second portion 40.

In the second form of the air-blowing device 10A illustrated in FIG. 4, the second portion 40 is farther from the bottom surface 34 of the first portion 33 compared with the first form. More specifically, the bottom surface 34 of the first portion 33 and the top wall 41 of the second portion 40 are farthest from each other within the relative movement range of the first portion 33 and the second portion 40 in the heightwise direction Z. In other words, in the second form of the air-blowing device 10A, the volume of the air-blowing chamber 32A, which is the enclosed space surrounded by the first portion 33 and the second portion 40, is largest. In the second form of the air-blowing device 10A, only upper end portions of the partition wall 31 and the first side wall 35 of the first portion 33 are accommodated in the space surrounded by the top wall 41 and the side wall 42 of the second portion 40. In other words, in the second form of the air-blowing device 10A, the partition wall 31 and the first side wall 35 of the first portion 33, which are accommodated in the space surrounded by the top wall 41 and the side wall 42 of the second portion 40 in the first form, project from the second portion 40.

When the patient P uses the fluid control apparatus 1, the patient P slides upward the second portion 40 of the air-blowing device 10A that is in the first form illustrated in FIG. 3A so as to change the form of the air-blowing device 10A to the second form illustrated in FIG. 4. After that, the patient P wears the mask 12 (see FIG. 1) and operates the operation unit 22 so as to drive the air blower 50. As a result, as indicated by bold line arrows in FIG. 4, the air outside the air-blowing device 10A flows into the air-blowing chamber 32A through the intake hole 41a. The air that has flowed in the air-blowing chamber 32A flows into the case 53 through the suction port 53a, which is formed in the case 53 of the air blower 50, and is discharged to the discharge port 53b as a result of rotation of the impeller 52. The air discharged from the discharge port 53b is supplied to the mask 12 through the exhaust portion 35a and the tube 11 (see FIG. 1).

After the patient P has used the fluid control apparatus 1, the patient P slides the second portion 40 toward the first portion 33 such that the top wall 41 of the second portion 40 comes close to the bottom surface 34 of the first portion 33, so that the second form of the air-blowing device 10A is changed to the first form.

Effects of the present embodiment will be described.

In order to reduce the noise of the air-blowing device 10A, it is preferable to increase the transmission loss in the air-blowing device 10A. The degree of increase in the transmission loss becomes large as the volume of the air-blowing chamber 32A with respect to the opening area of the intake hole 41a increases. Accordingly, conceivable methods for increasing the transmission loss may be a first method in which the opening area of the intake hole 41a is reduced and a second method in which the volume of the air-blowing chamber 32A is increased. In the first method, the flow resistance when the air passes through the intake hole 41a increases, and thus, there is a possibility that the discharge flow rate of the air blower 50 will be reduced. In order to prevent a decrease in the discharge flow rate of the air blower 50, it may be considered to increase the rotational speed of the air blower 50. However, the noise increases as the rotational speed of the air blower 50 increases. In contrast, in the second method, the flow resistance when the air passes through the intake hole 41a does not increase, and thus, it is not necessary to increase the rotational speed of the air blower 50. Therefore, the noise of the air blower 50 can be prevented from increasing. However, if the volume of the air-blowing chamber 32A is kept large, the size of the air-blowing device 10A is large at all times, and for example, when the patient P carries the air-blowing device 10A while the air blower 50 is not driven, it is difficult for the patient P to put the air-blowing device 10A in a bag or the like.

Accordingly, when the patient P uses the air-blowing device 10A of the present embodiment, the form of the air-blowing device 10A is changed from the first form to the second form, and when the air-blowing device 10A is not in use, the form of the air-blowing device 10A is changed from the second form to the first form. As a result, the volume of the air-blowing chamber 32A, which is the space surrounded by the first portion 33 and the second portion 40, when the air-blowing device 10A is in use becomes larger than the volume of the air-blowing chamber 32A in the first form by the volume of a portion that is illustrated by half-tone shading in FIG. 4. In other words, the air-blowing chamber 32A forms an expandable silencer. Consequently, when the air blower 50 is driven, the noise of the air blower 50 propagates to the air-blowing chamber 32A that has been expanded, and thus, the transmission loss increases. Therefore, the noise of the air-blowing device 10A can be reduced. In addition, when the air-blowing device 10A is not in use, the housing 20 is smaller in size than that during the period when the air-blowing device 10A is being used, and this makes it easier for the patient P to put the air-blowing device 10A in a bag or the like when the patient P carries the air-blowing device 10A.

As described above, according to the present embodiment, the following advantageous effects are obtained.

(1-1) In the air-blowing device 10A, the housing 20 is configured to be capable of expanding and contracting so as to change the internal volume of the housing 20. Thus, the air-blowing device 10A is brought into the second form when the air blower 50 is driven, and the housing 20 is expanded such that the internal volume of the housing 20 increases, and as a result, a decrease in the quietness of the air-blowing device 10A and the fluid control apparatus 1 when in use can be suppressed. In addition, when the air blower 50 is not driven, that is, for example, when the patient P carries the air-blowing device 10A, the air-blowing device 10A is brought into the first form, so that the housing 20 is contracted, and the internal volume of the housing 20 decreases. As a result, the housing 20 becomes small in size, and thus, the portability of the air-blowing device 10A and the fluid control apparatus 1 when not in use can be improved.

(1-2) By increasing the volume of the internal space of the housing 20, which is surrounded by the first portion 33 and the second portion 40, when the air blower 50 is driven, a silencing effect corresponding to the amount by which the volume of the internal space increases can be obtained. Thus, a decrease in the quietness of the air-blowing device 10A and the fluid control apparatus 1 when in use can be suppressed. In addition, when the air blower 50 is not driven, that is, for example, when the patient P carries the air-blowing device 10A and the fluid control apparatus 1, the housing 20 becomes small in size by reducing the volume of the internal space surrounded by the first portion 33 and the second portion 40. Therefore, the portability of the air-blowing device 10A and the fluid control apparatus 1 when not in use can be improved.

(1-3) The volume of the internal space of the housing 20 surrounded by the first portion 33 and the second portion 40 can be easily changed by causing the first portion 33 and the second portion 40 to move relative to each other.

(1-4) In the first form of the air-blowing device 10A, the partition wall 31 and the first side wall 35 of the first portion 33 are accommodated in the space surrounded by the top wall 41 and the side wall 42 of the second portion 40. As a result, the reduction in the size of the housing 20 in the first form can be further facilitated compared with a configuration in which the partition wall 31 and the first side wall 35 of the first portion 33 are not accommodated in the space surrounded by the top wall 41 and the side wall 42 of the second portion 40.

(1-5) The elastic member 38 that hermetically seals the gap between the first side wall 35 and the side wall 42 of the second portion 40 is attached to the first side wall 35 of the first portion 33. Thus, the probability of the air in the air-blowing chamber 32A leaking to the outside of the housing 20 through the gap between the first side wall 35 and the side wall 42 can be reduced. Therefore, a decrease in flow-rate characteristics of the air-blowing device 10A can be suppressed.

(1-6) The display unit 21 and the operation unit 22 are mounted on the top wall 37 of the first portion 33. In other words, the display unit 21 and the operation unit 22 are each arranged at a portion other than the second portion 40, the portion being a portion of the main body 30 that is not covered with the second portion 40. Thus, the first control circuit board 23 and the second control circuit board 24 do not move relative to each other. Therefore, the electrical connection configuration between the first control circuit board 23 and the second control circuit board 24 can be further simplified, and the reliability of the electrical connection between the first control circuit board 23 and the second control circuit board 24 can be further improved compared with a configuration in which the display unit 21 and the operation unit 22 are mounted on the second portion 40, that is, a configuration in which the first control circuit board 23 and the second control circuit board 24 move relative to each other.

Second Embodiment

The air-blowing device 10A and the fluid control apparatus 1 according to the second embodiment will be described with reference to FIG. 5 and FIG. 6. The difference between the air-blowing device 10A and the fluid control apparatus 1 according to the second embodiment and the air-blowing device 10A and the fluid control apparatus 1 according to the first embodiment is that a partition-wall portion 60 is added to the first portion 33 in the second embodiment. Note that, in the present embodiment, components that are the same as those in the first embodiment are denoted by the same reference signs, and descriptions thereof will be suitably omitted. Descriptions of the relationships between the components that are the same as those in the first embodiment will also be suitably omitted.

Figure 5:
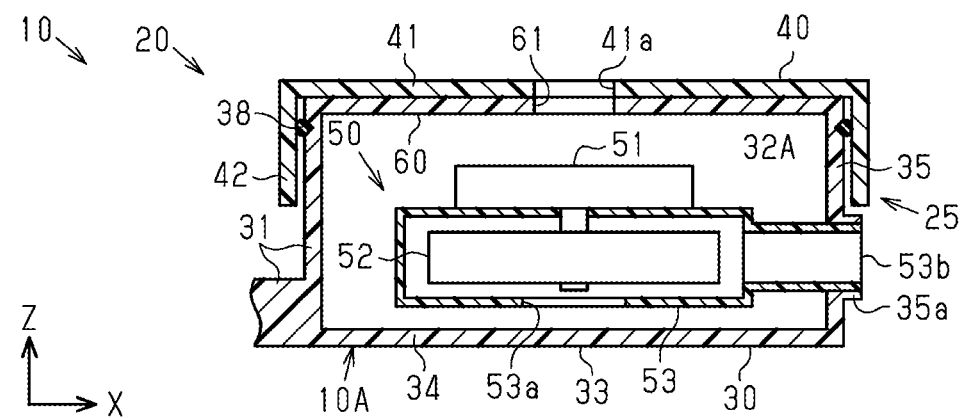
FIG. 5 is a sectional side view of an air-blowing device that is in the first form in a fluid control apparatus according to a second embodiment.

As illustrated in FIG. 5, the partition-wall portion 60 is formed on the upper end portions of the partition wall 31 and the first side wall 35 and faces the bottom surface 34, which is included in the air-blowing device 10A. The partition-wall portion 60 is integrally formed with the first portion 33 (the partition wall 31 and the first side wall 35). The air-blowing chamber 32A is formed of the partition-wall portion 60, the partition wall 31, the first side wall 35, and the bottom surface 34.

The partition-wall portion 60 has a communication portion 61 that allows the communication between the air-blowing chamber 32A and a space outside the air-blowing chamber 32A. An example of the communication portion 61 is a through hole that extends through the partition-wall portion 60 in the heightwise direction Z. An opening surface of the communication portion 61 faces an opening surface of the intake hole 41a of the second portion 40. The opening area of the communication portion 61 may be arbitrarily set. As an example, the opening area of the communication portion 61 is equal to the opening area of the intake hole 41a.

In the first form of the air-blowing device 10A illustrated in FIG. 5, the partition-wall portion 60 and the top wall 41 of the second portion 40 are close to each other. In FIG. 5, the partition-wall portion 60 and the top wall 41 are in contact with each other. Note that, in the first form of the air-blowing device 10A, a gap may be generated between the partition-wall portion 60 and the top wall 41 in the heightwise direction Z.

Figure 6:
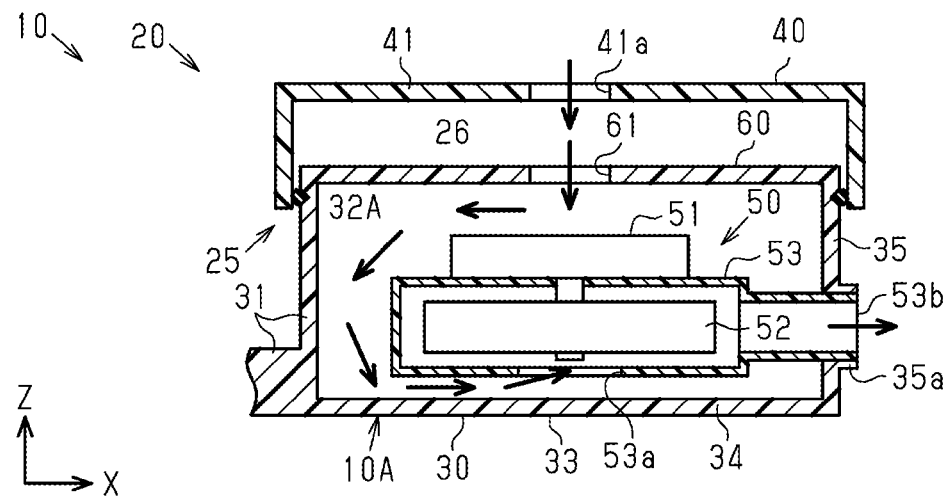
FIG. 6 is a sectional side view of the air-blowing device that is in the second form in the fluid control apparatus according to the second embodiment.

In the second form of the air-blowing device 10A illustrated in FIG. 6, by sliding the second portion 40 upward with respect to the first portion 33, the partition-wall portion 60 and the top wall 41 of the second portion 40 are separated from each other in the heightwise direction Z. As a result, in the housing 20, a silencer cavity 26 that is a space surrounded by the top wall 41 and the side wall 42 of the second portion 40 and the partition-wall portion 60 is formed. In other words, in the second form of the air-blowing device 10A, an expandable silencer is added to the air-blowing chamber 32A in the housing 20. In the second form of the air-blowing device 10A, the partition-wall portion 60 isolates the air-blowing chamber 32A and the silencer cavity 26 from each other.

In a state where the air blower 50 is driven, as indicated by the bold line arrows in FIG. 6, the air outside the air-blowing device 10A flows into the silencer cavity 26 through the intake hole 41a. The air that has passed through the intake hole 41a flows into the air-blowing chamber 32A through the silencer cavity 26 and the communication portion 61. The air that has flowed in from the air-blowing chamber 32A is sucked into the suction port 53a of the air blower 50. The air blower 50 supplies the air to the tube 11 (see FIG. 1) through the discharge port 53b.

As described above, according to the present embodiment, the following advantageous effects can be obtained in addition to the advantageous effects of the first embodiment.

(2-1) The housing 20 includes the partition-wall portion 60 that isolates the air-blowing chamber 32A and the silencer cavity 26 from each other. The partition-wall portion 60 includes the communication portion 61 that allows the communication between the air-blowing chamber 32A of the first portion 33 and the internal space of the second portion 40. The air blower 50, the first control circuit board 23, and the second control circuit board 24 (see FIG. 4) are not disposed in the silencer cavity 26. As a result, acoustic waves in the silencer cavity 26 are not reflected by the air blower 50, the first control circuit board 23, and the second control circuit board 24. Thus, the probability that the behavior of the acoustic waves in the silencer cavity 26 will become complex due to the acoustic waves in the silencer cavity 26 and their reflected waves generated by the air blower 50 can be reduced. This makes it easier to create the characteristics of a silencer in the silencer cavity 26. Consequently, designing of the silencer cavity 26 that may easily improve the quietness of the air-blowing device 10A is facilitated. Note that an example of the characteristics of a silencer is the relationship between transmission loss and frequency. By simplifying the behavior of the acoustic waves in the silencer cavity 26, the relationship between transmission loss and frequency is simplified.

(2-2) The opening surface of the intake hole 41a of the second portion 40 and the opening surface of the communication portion 61 of the partition-wall portion 60, the opening surface of the communication portion 61 being located on the side on which the second portion 40 is disposed, face each other. Thus, the reflection of the sound in the silencer cavity 26 is more predictable than that in a configuration in which the opening surface of the intake hole 41a and the opening surface of the communication portion 61 that is located on the side on which the second portion 40 is disposed do not face each other, and this makes it easier to create the characteristics of a silencer in the silencer cavity 26.

Third Embodiment

The air-blowing device 10A and the fluid control apparatus 1 according to the third embodiment will be described with reference to FIG. 7 to FIG. 10. In the air-blowing device 10A and the fluid control apparatus 1 according to the third embodiment, the configuration of the housing, particularly the direction of movement of the second portion with respect to the first portion, is different from that in the air-blowing device 10A and the fluid control apparatus 1 according to the first embodiment. Note that, in the present embodiment, components that are the same as those in the first embodiment are denoted by the same reference signs, and descriptions thereof will be suitably omitted. Descriptions of the relationships between the components that are the same as those in the first embodiment will also be suitably omitted.

Figure 7:
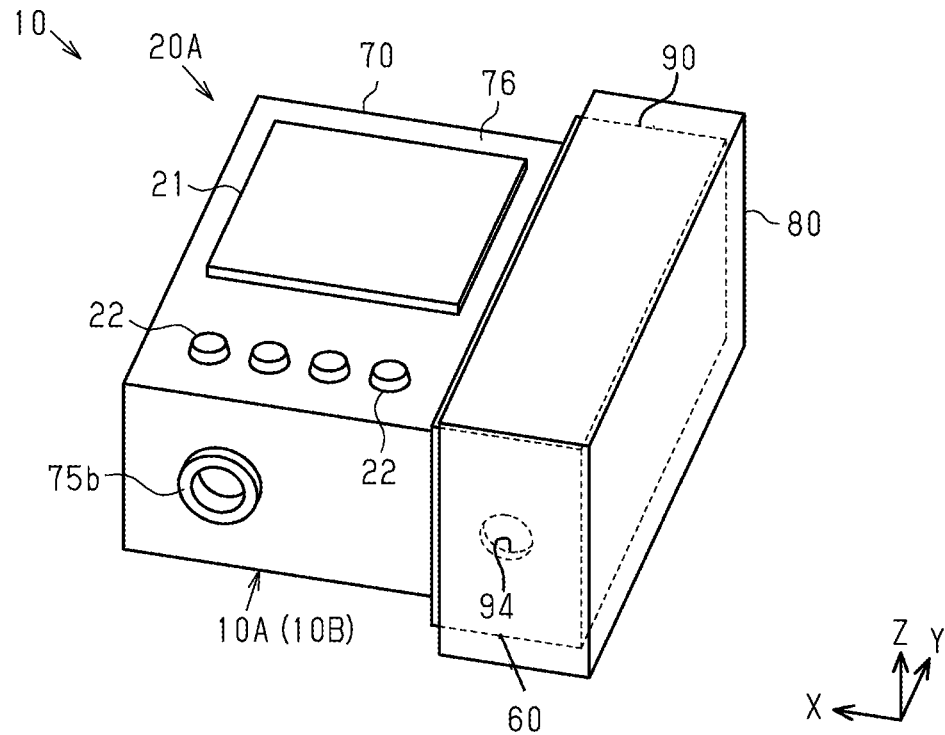
FIG. 7 is a perspective view of an air-blowing device that is in the first form in a fluid control apparatus according to a third embodiment.

As illustrated in FIG. 7, a housing 20A of the apparatus body 10 (the air-blowing device 10A) includes a first portion 70, a second portion 80, and the partition-wall portion 60. The partition-wall portion 60 includes a first partition-wall portion 75x (see FIG. 9) and a second partition-wall portion 90. The second partition-wall portion 90 is attached to the first portion 70, and the second portion 80 is attached to the second partition-wall portion 90. When the first form of the air-blowing device 10A illustrated in FIG. 7 is changed to the second form of the air-blowing device 10A illustrated in FIG. 8, the second partition-wall portion 90 is moved in the transverse direction X with respect to the first portion 70, and the second portion 80 is moved in the transverse direction X with respect to the second partition-wall portion 90.

Figure 9:
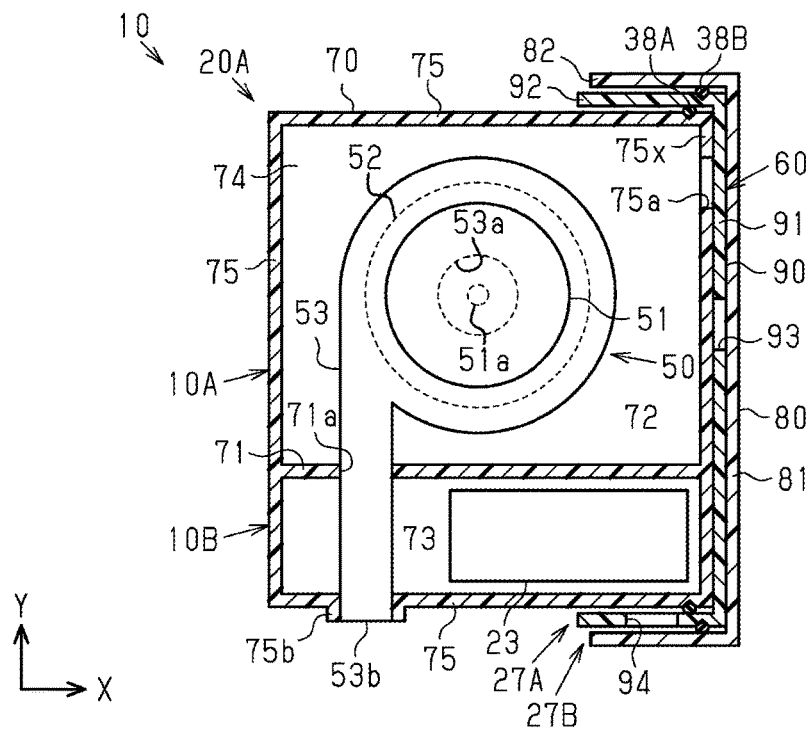
FIG. 9 is a plan sectional view of the air-blowing device when the air-blowing device is in the first form.

As illustrated in FIG. 9, an air-blowing chamber 72 and a control chamber 73 that are partitioned by a partition wall 71 are formed in the first portion 70. The air-blowing chamber 72 and the control chamber 73 are arranged in a longitudinal direction Y that is perpendicular to the transverse direction X and the heightwise direction Z. As described above, the control device 10B is accommodated in the first portion 70. When viewed in a plan view, the first portion 70 includes a bottom wall 74 having a rectangular shape, side walls 75 each extending from the outer peripheral edge of the bottom wall 74 in a direction away from the bottom wall 74, and a top wall 76 (see FIG. 7) opposing the bottom wall 74. The partition wall 71 extends across two of the side walls 75, the two side walls 75 opposing to each other in the transverse direction X. A through hole 71a is formed in the partition wall 71. The first partition-wall portion 75x is disposed between the first portion 70 and the second partition-wall portion 90 in the transverse direction X and extends in the longitudinal direction Y. The first partition-wall portion 75x isolates the air-blowing chamber 72 and the space inside the second portion 80 from each other. An inner intake hole 75a is formed in the first partition-wall portion 75x. One of the side walls 75 that forms a part of the control chamber 73 and that extends in the transverse direction X has an exhaust hole 75b that is an example of the second cavity. The exhaust hole 75b faces the through hole 71a in the longitudinal direction Y. A discharge-side portion of the case 53 of the air blower 50 that is disposed in the air-blowing chamber 72 is inserted in the through hole 71a and the exhaust hole 75b.

As illustrated in FIG. 7, the display unit 21 and the operation unit 22 are mounted on the top wall 76. The top wall 76 covers the air-blowing chamber 72 and the control chamber 73 from above. Thus, the area of the top wall 76 when viewed in a plan view is larger than the area of the top wall 37 of the housing 20 of each of the first and second embodiments when viewed in a plan view. Although not illustrated, the second control circuit board 24 is mounted on a portion of the bottom surface of the top wall 76, the portion corresponding to the air-blowing chamber 72 and the control chamber 73.

As illustrated in FIG. 9, the second partition-wall portion 90 is disposed between the first partition-wall portion 75x and the second portion 80. The second partition-wall portion 90 includes a side wall 91 facing one of the side walls 75 of the first portion 70 in the transverse direction X and a peripheral wall 92 extending from the outer peripheral edge of the side wall 91 in the transverse direction X toward the first portion 70. An outer intake hole 94 is formed in the peripheral wall 92. The opening area of the outer intake hole 94 may be arbitrarily set. As an example, the opening area of the outer intake hole 94 is equal to the opening area of the inner intake hole 75a. The side wall 91 has a communication portion 93. An example of the communication portion 93 is a through hole that extends through the side wall 91 in the transverse direction X. In the side wall 91, the communication portion 93 is located at a position that is closer to the outer intake hole 94 than a position facing the inner intake hole 75a is. The opening area of the communication portion 93 may be arbitrarily set. As an example, the opening area of the communication portion 93 is equal to the opening area of the inner intake hole 75a.

The second partition-wall portion 90 covers a right-hand end portion of the first portion 70. The peripheral wall 92 faces the two side walls 75 that extend in the transverse direction X, the bottom wall 74, and the top wall 76 with a gap formed between the peripheral wall 92 and each of the two side walls 75, the bottom wall 74, and the top wall 76. The peripheral wall 92 of the second partition-wall portion 90, the two side walls 75 of the first portion 70 that extend in the transverse direction X, the bottom wall 74, and the top wall 76 form a first movable unit 27A that is capable of performing a relative movement in the transverse direction X. An elastic member 38A that is used for hermetically sealing a space between the first portion 70 and the second partition-wall portion 90 is disposed between the peripheral wall 92, the two side walls 75 extend in the longitudinal direction X, the bottom wall 74, and the top wall 76. An example of the elastic member 38A is an O-ring. The elastic member 38A is attached to the first portion 70. Grease is applied to a surface of the peripheral wall 92 that faces the two side walls 75 that extend in the transverse direction X, the bottom wall 74, and the top wall 76.

The second portion 80 includes a side wall 81 facing the side wall 91 of the second partition-wall portion 90 in the transverse direction X and a peripheral wall 82 extending from the outer peripheral edge of the side wall 81 in the transverse direction X toward the second partition-wall portion 90. As seen from the second partition-wall portion 90, the second portion 80 covers the second partition-wall portion 90 from the side on which the first portion 70 is not located. In the first form of the air-blowing device 10A illustrated in FIG. 9, the peripheral wall 82 covers the outer intake hole 94. The peripheral wall 82 faces the peripheral wall 92 of the second partition-wall portion 90 with a gap formed therebetween. The peripheral wall 82 of the second portion 80 and the peripheral wall 92 of the second partition-wall portion 90 form a second movable unit 27B that is capable of performing a relative movement in the transverse direction X. An elastic member 38B that is used for hermetically sealing a space between the second partition-wall portion 90 and the second portion 80 is disposed between the peripheral wall 82 of the second portion 80 and the peripheral wall 92 of the second partition-wall portion 90. An example of the elastic member 38B is an O-ring. The elastic member 38A is attached to the second partition-wall portion 90. Grease is applied to a surface of the peripheral wall 82 of the second portion 80, the surface facing the peripheral wall 92 of the second partition-wall portion 90. Note that the first movable unit 27A and the second movable unit 27B form a movable unit that causes the first portion 70 and the second portion 80 to move relative to each other.

In the first form of the air-blowing device 10A illustrated in FIG. 9, the second partition-wall portion 90 is accommodated in a space surrounded by the side wall 81 and the peripheral wall 82 of the second portion 80, and the right-hand portion of the first portion 70 is accommodated in a space surrounded by the side wall 91 and the peripheral wall 92 of the second partition-wall portion 90. More specifically, the right-hand portion of the first portion 70 and the second partition-wall portion 90 is accommodated in the space surrounded by the side wall 81 and the peripheral wall 82 of the second portion 80. The outer intake hole 94 faces one of the side walls 75 and the peripheral wall 82. Thus, the outer intake hole 94 is not exposed to the outside of the housing 20A and is not in communication with the air-blowing chamber 72.

Figure 10:
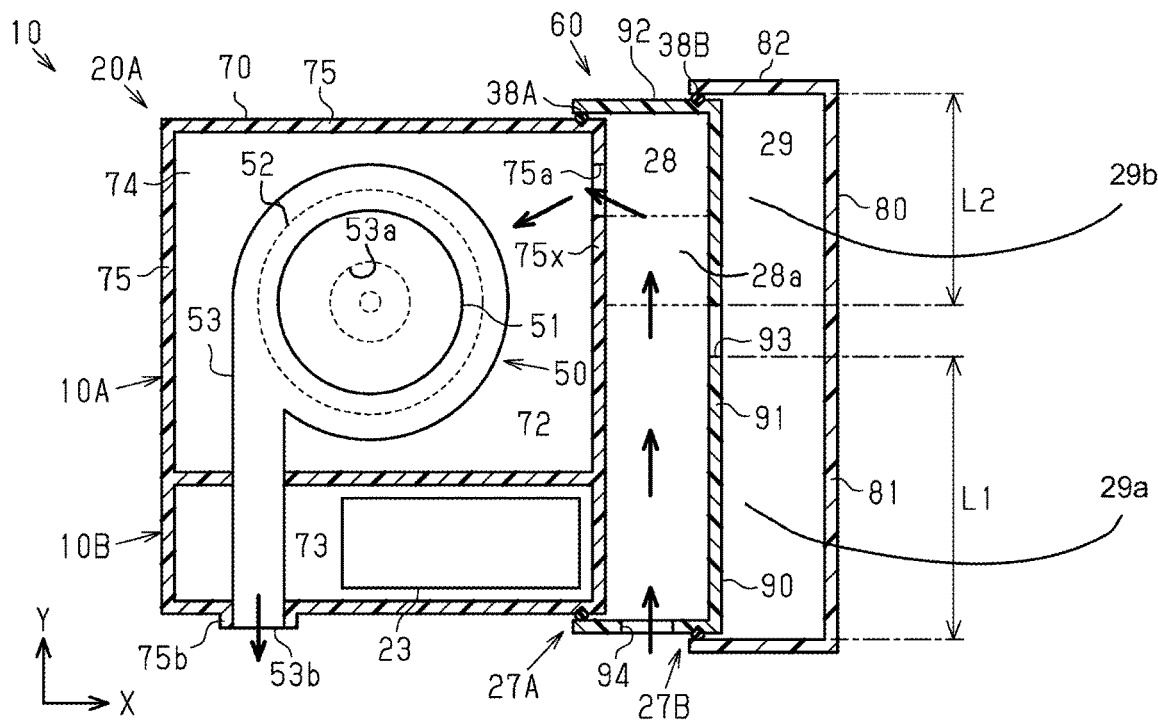
FIG. 10 is a plan sectional view of the air-blowing device when the air-blowing device is in the second form.

When the first form of the air-blowing device 10A illustrated in FIG. 9 is changed to the second form of the air-blowing device 10A illustrated in FIG. 10, the patient P (see FIG. 1) slides the second portion 80 in the transverse direction X. Along with this, the second partition-wall portion 90 slides in the transverse direction X. As a result, the second portion 80 and the second partition-wall portion 90 move away from the first portion 70 in the transverse direction X, and the second portion 80 moves away from the second partition-wall portion 90 in the transverse direction X. In other words, the right-hand portion of the first portion 70 that has been accommodated in the above-mentioned space in the first form of the air-blowing device 10A projects from the second partition-wall portion 90, and the second partition-wall portion 90 that has been accommodated in the above-mentioned space in the first form projects from the second portion 80.

As illustrated in FIG. 10, in the second form of the air-blowing device 10A, a suction path 28 is formed between the first partition-wall portion 75x and the second partition-wall portion 90. In other words, the suction path 28 is formed outside the first portion 70. In addition, in the second form of the air-blowing device 10A, the outer intake hole 94 is positioned outside the first portion 70 in the transverse direction X, and the peripheral wall 82 of the second portion 80 is positioned outside the outer intake hole 94 in the transverse direction X. Thus, the outer intake hole 94 is exposed to the outside of the housing 20A and is in communication with the suction path 28. The suction path 28 communicates with the air-blowing chamber 72, specifically, the suction port 53a of the air blower 50 via the inner intake hole 75a. Therefore, the suction path 28 allows the communication between the outer intake hole 94 and the suction port 53a.

A silencer cavity 29 that is a space surrounded by the side wall 91 of the second partition-wall portion 90 and the second portion 80 is formed between the second portion 80 and the second partition-wall portion 90. The silencer cavity 29 communicates with the suction path 28 via the communication portion 93. The silencer cavity 29 extends in the longitudinal direction Y so as to be parallel to the suction path 28. In other words, in the second form of the air-blowing device 10A, the housing 20A includes a branched silencer. The silencer cavity 29 includes a first cavity 29a extending in the longitudinal direction of the silencer cavity 29 from the communication portion 93 toward the side on which the outer intake hole 94 is present and a second cavity 29b extending in the longitudinal direction of the silencer cavity 29 from the communication portion 93 toward the side on which the inner intake hole 75a is present. In the longitudinal direction of the silencer cavity 29, a length L1 of the first cavity 29a and a length L2 of the second cavity 29b are different from each other. As illustrated in FIG. 10, the length L1 of the first cavity 29a is longer than the length L2 of the second cavity 29b. In the second form of the air-blowing device 10A according to the present embodiment, the passage cross-sectional area of the silencer cavity 29, the length L1 of the first cavity 29a, and the length L2 of the second cavity 29b are set such that, among the noise of the air-blowing device 10A, acoustic waves of two different specific frequencies within a frequency range of 1,000 kHz or higher and 5,000 kHz or lower can be effectively reduced. Note that the length L1 of the first cavity 29a and the length L2 of the second cavity 29b may be arbitrarily changed in accordance with the noise of the frequency to be reduced. For example, the length L1 of the first cavity 29a may be shorter than the length L2 of the second cavity 29b.

Effects of the present embodiment will be described.

When the air blower 50 is driven while the air-blowing device 10A is in the second form, rotating noise (predominant sound) of the impeller 52 is generated. The frequency of the predominant sound is calculated on the basis of the product of the rotational speed of the impeller 52 and the number of blades of the impeller 52. The predominant sound propagates to the outside of the housing 20 through the air-blowing chamber 32A, the suction path 28, and the outer intake hole 94. Here, the predominant sound that has propagated from the air-blowing chamber 32A to the suction path 28 propagates through a passage 28a that is formed between the inner intake hole 75a and the communication portion 93 in the suction path 28 and propagates to the silencer cavity 29 through the communication portion 93. Here, the passage cross-sectional area of the passage 28a is constant, and thus, acoustic waves of the predominant sound propagating through the passage 28a gradually change to plane waves. The predominant sound in the form of plane waves branches and propagates to the first cavity 29a and the second cavity 29b of the silencer cavity 29 through the communication portion 93. The predominant sound that has propagated to the first cavity 29a is reflected by the peripheral wall 82 of the second portion 80, which is an end wall of the first cavity 29a, and returns to the communication portion 93. The predominant sound that has propagated to the second cavity 29b is reflected by the peripheral wall 82 of the second portion 80, which is an end wall of the second cavity 29b, and returns to the communication portion 93. The predominant sound that has returned to the suction path 28 from the communication portion 93 is superimposed with the predominant sound in the suction path 28, so that they cancel each other out.

Here, the length L1 of the first cavity 29a is set to have a phase that cancels out the predominant sound at a first rotational speed of the motor 51 (the impeller 52) of the air blower 50, that is, a phase opposite to the phase of the predominant sound in the suction path 28. The length L2 of the second cavity 29b is set to have a phase that cancels out the predominant sound at a second rotational speed that is different from the first rotational speed of the motor 51 (the impeller 52). Thus, the predominant sound that is generated when the air blower 50 is driven at the first rotational speed or the second rotational speed is reduced. Note that the frequency of the predominant sound at the first rotational speed and the frequency of the predominant sound at the second rotational speed are each set within a range of 1,000 kHz or higher and 5,000 kHz or lower.

As described above, according to the present embodiment, the following advantageous effects are obtained.

(3-1) The suction path 28 is formed between the first partition-wall portion 75x and the second partition-wall portion 90, and the silencer cavity 29 is formed between the second partition-wall portion 90 and the second portion 80. Accordingly, the silencer cavity 29 is formed outside the air-blowing chamber 72, and thus, the silencer cavity 29 becomes a space dedicated to a silencer. Therefore, the silencing effect is improved by the silencer cavity 29, and a decrease in the quietness of the air-blowing device 10A and the fluid control apparatus 1 can be suppressed.

(3-2) The passage cross-sectional area of the passage 28a of the suction path 28 is constant. Thus, the acoustic waves of the predominant sound that propagates through the passage 28a become plane waves. As a result, the predominant sound that propagates to the suction path 28 is likely to be cancelled out by the first cavity 29a and the second cavity 29b of the silencer cavity 29.

(3-3) In the first form of the air-blowing device 10A, the peripheral wall 82 of the second portion 80 covers the outer intake hole 94 of the second partition-wall portion 90. Thus, foreign substances such as dust are less likely to enter the space between the first portion 70 and the second partition-wall portion 90, and the air-blowing chamber 72 through the outer intake hole 94.

(3-4) The second partition-wall portion 90 is attached to the first portion 70 so as to be movable relative to the first portion 70. As a result, the volume of the suction path 28 can be changed, and thus, when the air blower 50 is not driven, that is, for example, when the patient P carries the air-blowing device 10A and the fluid control apparatus 1, the volume of the suction path 28 can be reduced. Accordingly, the size of the housing 20A is reduced, and thus, the portability of the air-blowing device 10A and the fluid control apparatus 1 when not in use can be improved.

(3-5) The direction of movement of the second partition-wall portion 90 with respect to the first portion 70 and the direction of movement of the second portion 80 with respect to the second partition-wall portion 90 are the same direction, and thus, the patient P moves the second partition-wall portion 90 and the second portion 80 in one predetermined direction, so that the suction path 28 and the silencer cavity 29 are formed. Therefore, an operation for forming the suction path 28 and the silencer cavity 29 may be easily performed by the patient P.

(3-6) The space between the side walls 75 of the first portion 70 and the peripheral wall 92 of the second partition-wall portion 90 is sealed by the elastic member 38A. Thus, the probability of the air leaking from the air-blowing chamber 72 and the suction path 28 to the outside of the housing 20 can be reduced. In addition, the space between the peripheral wall 92 of the second partition-wall portion 90 and the peripheral wall 82 of the second portion 80 is sealed by the elastic member 38B. Thus, the probability of the air leaking from the silencer cavity 29 to the outside of the housing 20A can be reduced. Therefore, a decrease in the flow-rate characteristics of the air-blowing device 10A can be suppressed.

(3-7) In the first form of the air-blowing device 10A, the second partition-wall portion 90 and the right-hand portion of the first portion 70 are accommodated in the space surrounded by the side wall 81 and the peripheral wall 82 of the second portion 80. Thus, the reduction in the size of the housing 20A in the first form can be further facilitated compared with a configuration in which the second partition-wall portion 90 and the right-hand portion of the first portion 70 are not accommodated in the space surrounded by the side wall 81 and the peripheral wall 82 of the second portion 80.

Fourth Embodiment

The air-blowing device 10A and the fluid control apparatus 1 according to the fourth embodiment will be described with reference to FIGS. 11A and 11B and FIGS. 12A and 12B. The difference between the air-blowing device 10A and the fluid control apparatus 1 according to the fourth embodiment and the air-blowing device 10A and the fluid control apparatus 1 according to the third embodiment is that a partition unit 100 is added to the second portion 80 in the fourth embodiment. Note that, in the present embodiment, components that are the same as those in the third embodiment are denoted by the same reference signs, and descriptions thereof will be suitably omitted. Descriptions of the relationships between the components that are the same as those in the third embodiment will also be suitably omitted.

Figure 12A:
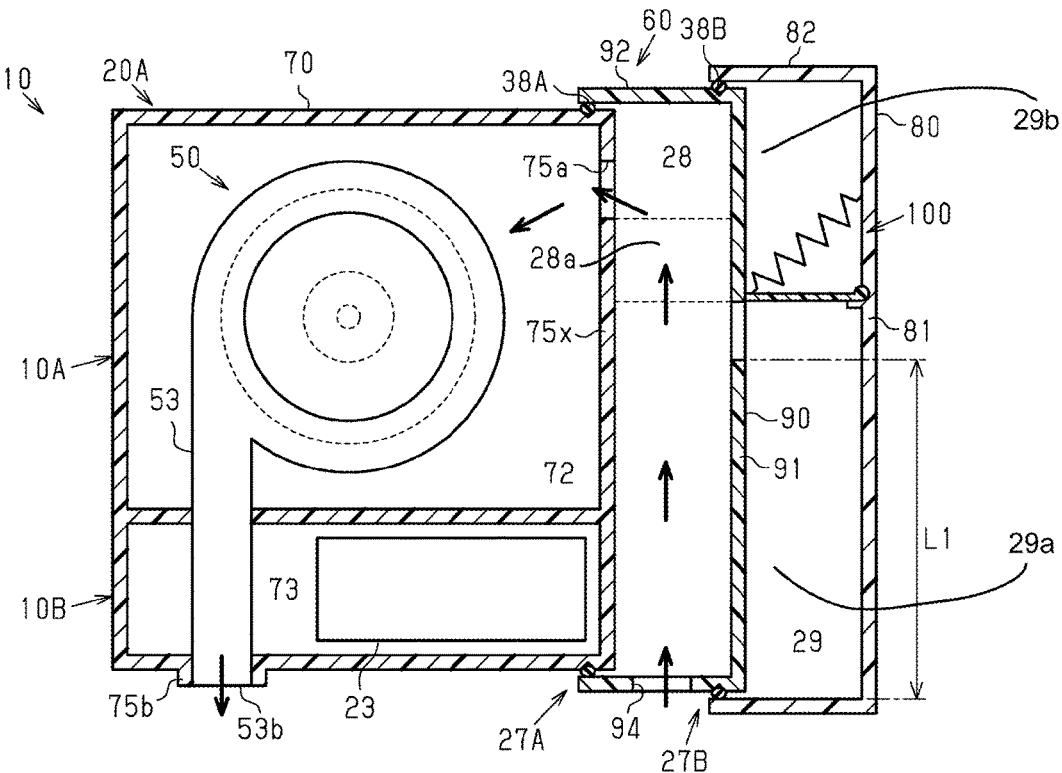
FIG. 12A is a plan sectional view of the air-blowing device when the air-blowing device is in the second form.
Figure 12B:
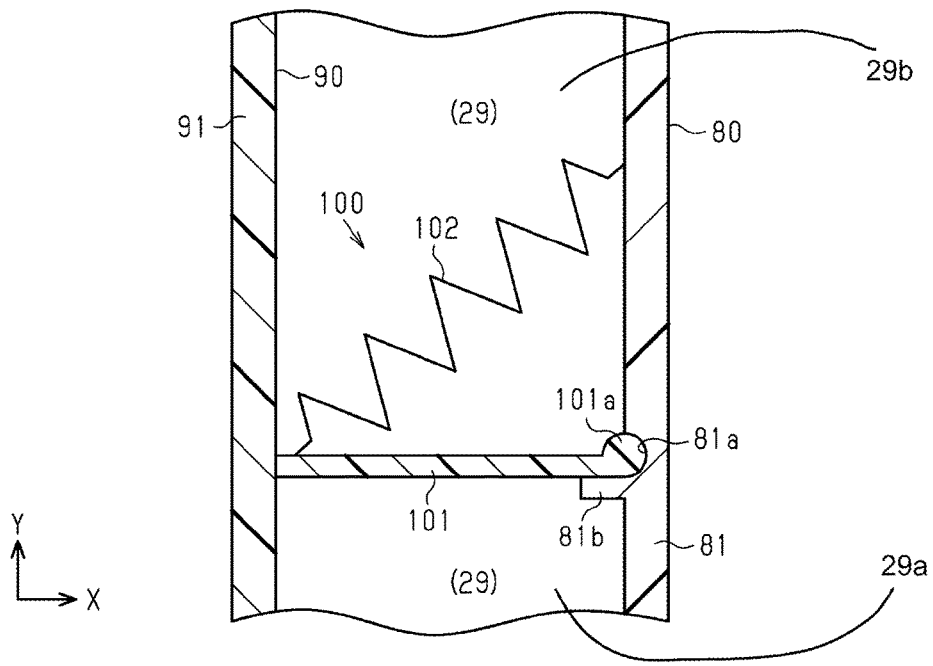
FIG. 12B is an enlarged view of the partition unit and the peripheral portion.

As illustrated in FIG. 12A, the silencer cavity 29 in the second form of the air-blowing device 10A the first cavity 29a, which is the space located on the side on which the outer intake hole 94 is present in the longitudinal direction Y, and the second cavity 29b, which is the space located on the side on which the inner intake hole 75a is present in the longitudinal direction Y. As illustrated in FIG. 12B, the partition unit 100 includes a partition plate 101 that is pivotable and an elastic body 102 that urges the partition plate 101 in a direction in which the partition plate 101 pivots. A pivot shaft 101a of the partition plate 101 is attached to a recess 81a of the second portion 80. A restricting portion 81b that restricts the pivotal movement of the partition plate 101 is provided at the recess 81a. An example of the restricting portion 81b is a protrusion that protrudes from the recess 81a to a pivotal-movement path of the partition plate 101. An example of the elastic body 102 is a coil spring. A first end portion of the elastic body 102 is attached to the partition plate 101, and a second end portion of the elastic body 102 is attached to the side wall 81 of the second portion 80.

Figure 11A:
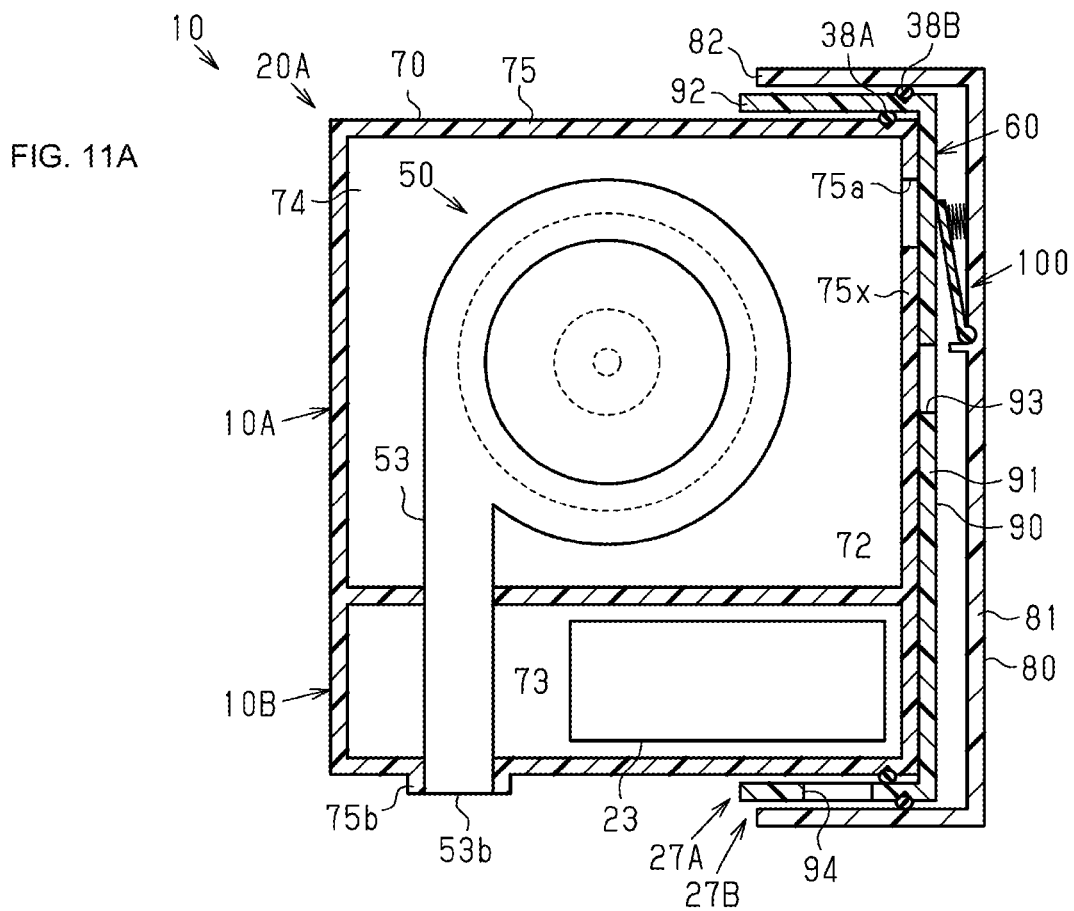
FIG. 11A is a plan sectional view of an air-blowing device in a fluid control apparatus according to a fourth embodiment when the air-blowing device is in the first form.
Figure 11B:
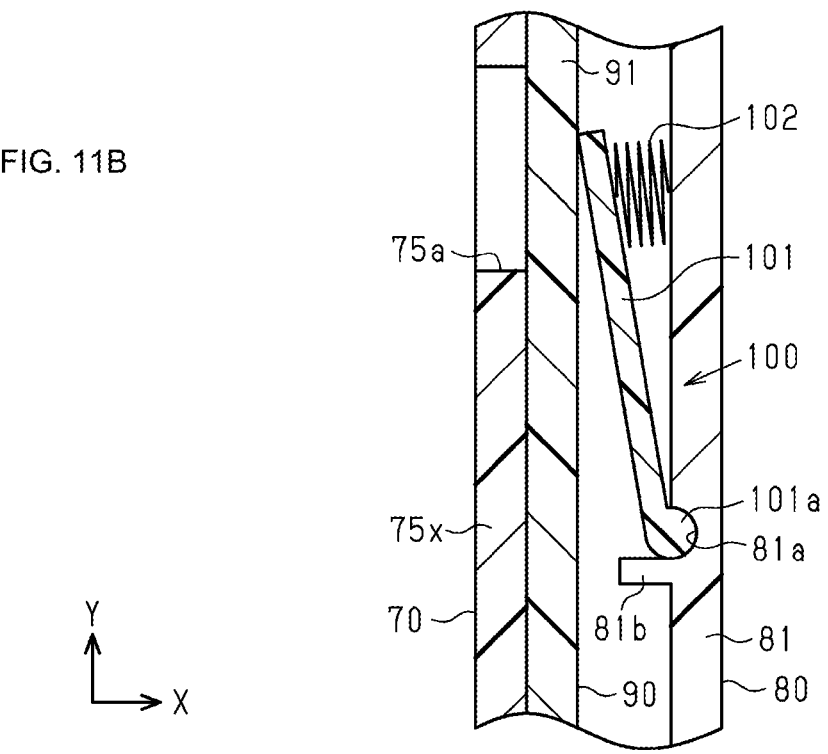
FIG. 11B is an enlarged view of a partition unit and the peripheral portion in the fluid control apparatus according to the fourth embodiment.

In the first form of the air-blowing device 10A illustrated in FIG. 11A and FIG. 11B, the partition unit 100 is pressed toward the side wall 81 of the second portion 80 by the side wall 91 of the second partition-wall portion 90, and thus, the elastic body 102 is in a state of being strongly compressed by the partition plate 101. In the second form of the air-blowing device 10A illustrated in FIG. 12A and FIG. 12B, as a result of the side wall 81 of the second portion 80 moving away from the side wall 91 of the second partition-wall portion 90, the partition plate 101 of the partition unit 100 is caused to pivot by an urging force of the elastic body 102. Then, the pivotal movement of the partition plate 101 is restricted by the restricting portion 81b. In the air-blowing device 10A of the present embodiment, the passage cross-sectional area and the length L1 of the first cavity 29a of the silencer cavity 29 are set such that, among the noise of the air-blowing device 10A in the second form, acoustic waves of one specific frequency within a frequency range of 1,000 kHz or higher and 5,000 kHz or lower can be effectively reduced. Note that, in the second form of the air-blowing device 10A, a gap may be formed between the partition plate 101 and the side wall 91 of the second partition-wall portion 90.

Effects of the present embodiment will be described.

In the case where the air blower 50 is driven while the air-blowing device 10A is in the second form, when the predominant sound generated by the air blower 50 propagates to the silencer cavity 29 through the communication portion 93, the predominant sound is less likely to propagate to the second cavity 29b of the silencer cavity 29 due to the partition plate 101. Thus, the predominant sound propagates to the first cavity 29a and is reflected by the peripheral wall 82 of the second portion 80, which is an end wall of the first cavity 29a so as to return to the suction path 28 through the communication portion 93. The predominant sound that has returned to the suction path 28 and the predominant sound in the suction path 28 cancel each other out.

As described above, according to the present embodiment, the following advantageous effects can be obtained in addition to the advantageous effects of the third embodiment.

(4-1) By providing the partition unit 100, the predominant sound of the air blower 50 at the first rotational speed is cancelled out by the first cavity 29a of the silencer cavity 29. Therefore, only the predominant sound at a specific target frequency can be reduced.

Fifth Embodiment

The air-blowing device 10A and the fluid control apparatus 1 according to the fifth embodiment will be described with reference to FIG. 13 and FIGS. 14A and 14B. The differences between the air-blowing device 10A and the fluid control apparatus 1 according to the fifth embodiment and the air-blowing device 10A and the fluid control apparatus 1 according to the first embodiment are that a housing in the fifth embodiment has a configuration different from the configuration of the housing in the first embodiment and that an external silencer is added to the housing in the fifth embodiment. Note that, in the present embodiment, components that are the same as those in the first embodiment are denoted by the same reference signs, and descriptions thereof will be suitably omitted. Descriptions of the relationships between the components that are the same as those in the first embodiment will also be suitably omitted.

As illustrated in FIG. 13, the air-blowing device 10A includes a housing 20B. The housing 20B includes a main body 30A and a silencer 110. The silencer 110 is detachably attached to the main body 30A. As an example, the silencer 110 is attached to the exhaust portion 35a of the main body 30A as illustrated in FIG. 13. The exhaust portion 35a of the main body 30A has an external thread 35c that is formed on the outer peripheral portion of the exhaust portion 35a and that is used for attaching the silencer 110 to the exhaust portion 35a. Note that the silencer 110 may be attached to an intake hole 39x instead of the exhaust portion 35a. In this case, the intake hole 39x has a configuration similar to that of the exhaust portion 35a.

The main body 30A includes a top wall 39A and a side wall 39B. The intake hole 39x that is an example of the first cavity and the exhaust portion 35a that is an example of the second cavity are formed in the side wall 39B. The main body 30A has an internal space that is hermetically sealed by the top wall 39A, the side wall 39B, and a bottom wall (not illustrated). The internal space is partitioned by the partition wall 31 into the air-blowing chamber 32A and the control chamber 32B as in the main body 30 of the first embodiment (see FIG. 3B). In addition, similar to the first portion 33 of the first embodiment, the air blower 50 is disposed in the air-blowing chamber 32A, and the first control circuit board 23 is disposed in the control chamber 32B (see FIG. 3B). The second control circuit board 24 (see FIG. 3A) is mounted on the bottom surface of the top wall 39A. As illustrated in FIG. 13, the display unit 21 and the operation unit 22 are mounted on the top wall 39A. Note that, in the main body 30A of the present embodiment, the air-blowing chamber 32A and the control chamber 32B are arranged in the longitudinal direction Y like the air-blowing chamber 72 and the control chamber 73 of the third embodiment. As in the third embodiment, the case 53 of the air blower 50 is inserted in a through hole (not illustrated) formed in the partition wall 31 and is attached to the exhaust portion 35a.

The silencer 110 is formed in a substantially cylindrical shape that has a cavity extending therethrough in the longitudinal direction. The silencer 110 includes a first connecting portion 112 having an internal thread 111 that is screwed onto the external thread 35c of the main body 30A, a second connecting portion 113 to be connected to the tube 11 (see FIG. 1), and a movable unit 114 connecting the first connecting portion 112 and the second connecting portion 113 to each other. The movable unit 114 connects the first connecting portion 112 and the second connecting portion 113 to each other while being capable of hermetically sealing the space between the first connecting portion 112 and the second connecting portion 113 and being capable of expanding and contracting. Thus, the movable unit 114 connects the first connecting portion 112 and the second connecting portion 113 to each other such that the first connecting portion 112 and the second connecting portion 113 are capable of moving toward and away from each other in the longitudinal direction of the silencer 110. An example of the shape of the movable unit 114 is a pleated shape.

The form of the air-blowing device 10A can be changed to the first form illustrated in FIG. 14A and the second form illustrated in FIG. 14B. As illustrated in FIG. 14A, in the first form of the air-blowing device 10A, the movable unit 114 of the silencer 110 is in a contracted state, that is, the volume of the internal space of the silencer 110 is small. As illustrated in FIG. 14B, in the second form of the air-blowing device 10A, the movable unit 114 of the silencer 110 is in an extended state, that is, the volume of the internal space of the silencer 110 is large.

As described above, according to the present embodiment, the following advantageous effects are obtained.

(5-1) When the air blower 50 is driven, the movable unit 114 of the silencer 110 is expanded, so that the volume of the internal space of the silencer 110 increases, and a cavity is formed inside the silencer 110. This cavity has a function of serving as a silencer, and thus, a decrease in the quietness of the air-blowing device 10A and the fluid control apparatus 1 when in use can be suppressed. In addition, when the air blower 50 is not driven, that is, for example, when the patient P carries the air-blowing device 10A and the fluid control apparatus 1, the patient P detaches the silencer 110 from the main body 30A and contracts the movable unit 114 of the silencer 110, so that the volume of the silencer 110 is reduced. As a result, the size of the housing 20B is reduced, and thus, the portability of the air-blowing device 10A and the fluid control apparatus 1 when not in use can be improved.

(Modifications)

The above descriptions of the embodiments are examples of possible aspects of the air-blowing device and the fluid control apparatus of the present disclosure and are not intended to limit the aspects. For example, the air-blowing device and the fluid control apparatus of the present disclosure each can take modifications of the embodiments that will be described below and a form obtained by combining at least two modifications that are not inconsistent with each other.

In the first and second embodiments, the configuration of the movable unit 25 may be arbitrarily changed. For example, the configuration of the movable unit 25 may be changed as in the following (A1) and (A2).

Figure 15A:
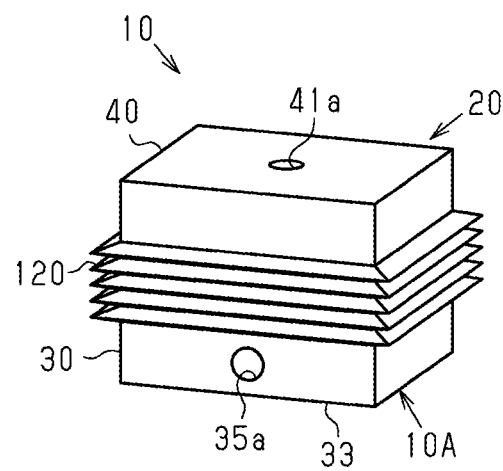
FIG. 15A is a perspective view of an air-blowing device in a fluid control apparatus according to a modification when the air-blowing device is in the first form.
Figure 15B:
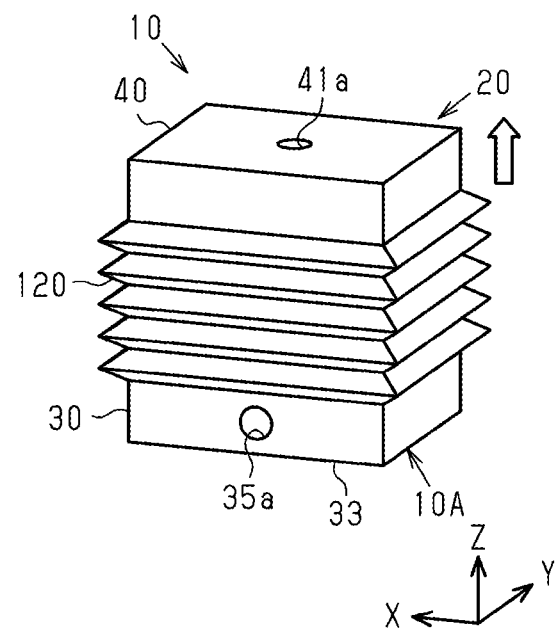
FIG. 15B is a perspective view of the air-blowing device in the fluid control apparatus according to the modification when the air-blowing device is in the second form.

(A1) As illustrated in FIG. 15A, a movable unit 120 connects the first portion 33 and the second portion 40 to each other in the heightwise direction Z and has a pleated structure that is capable of expanding and contracting in the heightwise direction Z. In the first form of the air-blowing device 10A illustrated in FIG. 15A, the movable unit 120 contracts by being compressed. As a result, the first portion 33 and the second portion 40 are close to each other. In the second form of the air-blowing device 10A illustrated in FIG. 15B, the movable unit 120 expands by being pulled. As a result, the first portion 33 and the second portion 40 are spaced apart from each other. In the second form of the air-blowing device 10A, the internal volume of the housing 20 is increased by the amount by which the movable unit 120 expands from the state of the movable unit 120 in the first form. In contrast, in the first form of the air-blowing device 10A, the size of the outline of the housing 20 is reduced by the amount by which the movable unit 120 contracts from the state of the movable unit 120 in the second form. As a result, advantageous effects similar to those of the first embodiment (1-1) are obtained.

Figure 16A:
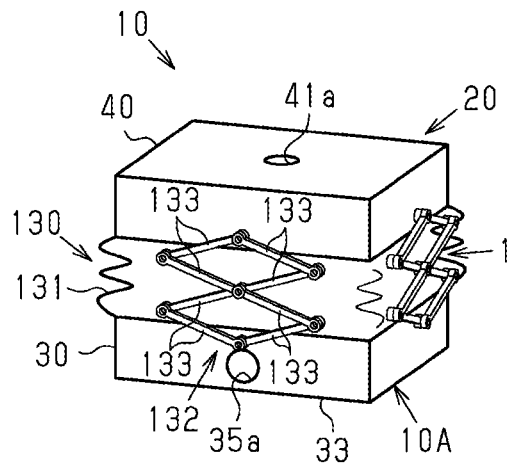
FIG. 16A is a perspective view of an air-blowing device in a fluid control apparatus according to another modification when the air-blowing device is in the first form.
Figure 16B:
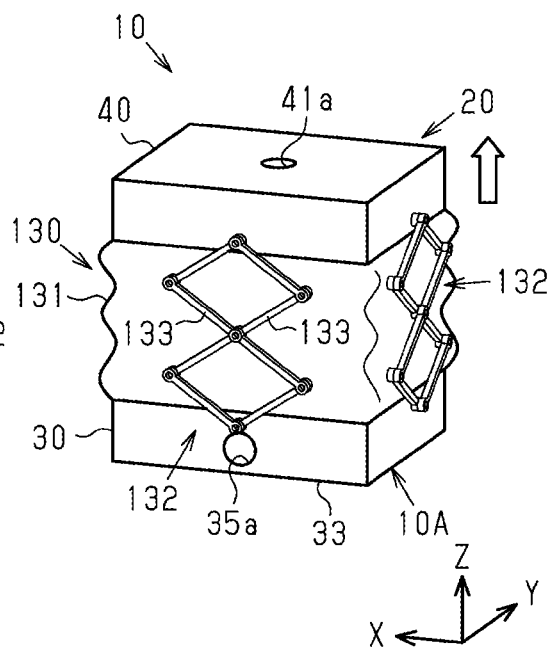
FIG. 16B is a perspective view of the air-blowing device in the fluid control apparatus according to this modification when the air-blowing device is in the second form.

(A2) As illustrated in FIG. 16A, a movable unit 130 connects the first portion 33 and the second portion 40 to each other in the heightwise direction Z and is capable of expanding and contracting in the heightwise direction Z. The movable unit 130 includes a soft portion 131 that is foldable and a plurality of guide mechanisms 132 (four guide mechanisms 132 in FIGS. 16A and 16B) that guide the folding operation of the soft portion 131 and support the second portion 40. The soft portion 131 is made of, for example, silicone rubber. The guide mechanisms 132 are mounted on the first side wall 35 of the first portion 33 and the side wall 42 of the second portion 40. As an example, each of the guide mechanisms 132 includes eight columns 133 that are connected to one another so as to form two diamond shapes illustrated in FIG. 16B. The columns 133 are pivotably connected to the other columns 133 at the two ends thereof. In the first form of the air-blowing device 10A illustrated in FIG. 16A, the first portion 33 and the second portion 40 are close to each other, and thus, the diamond shapes formed by the guide mechanisms 132 are collapsed. In the second form of the air-blowing device 10A illustrated in FIG. 16B, the first portion 33 and the second portion 40 are spaced apart from each other, and thus, the guide mechanisms 132 form the two diamond shapes. The guide mechanisms 132 hold the positions of the columns 133 illustrated in FIG. 16A and the positions of the columns 133 illustrated in FIG. 16B by, for example, a frictional force generated at pivotable portions of the columns 133.

In the third embodiment, the positional relationship between the inner intake hole 75a and the communication portion 93 may be arbitrarily changed. As an example, the opening surface of the inner intake hole 75a and the opening surface of the communication portion 93 may face each other. In this case, as illustrated in FIG. 17B, in the second form of the air-blowing device 10A, it is preferable that the housing 20A include an extension passage 140 that is used for changing the waves of the predominant sound that propagates from the air-blowing chamber 72 to the communication portion 93 to plane waves. The extension passage 140 extends from the inner intake hole 75a of the suction path 28 toward the air-blowing chamber 72. The passage cross-sectional area of the extension passage 140 can be arbitrarily set. As an example, the passage cross-sectional area of the extension passage 140 is equal to the passage cross-sectional area of the suction path 28. The extension passage 140 communicates with the silencer cavity 29. In other words, the communication portion 93 of the second partition-wall portion 90 is provided at a position facing the inner intake hole 75a in the transverse direction X.

Figure 8:
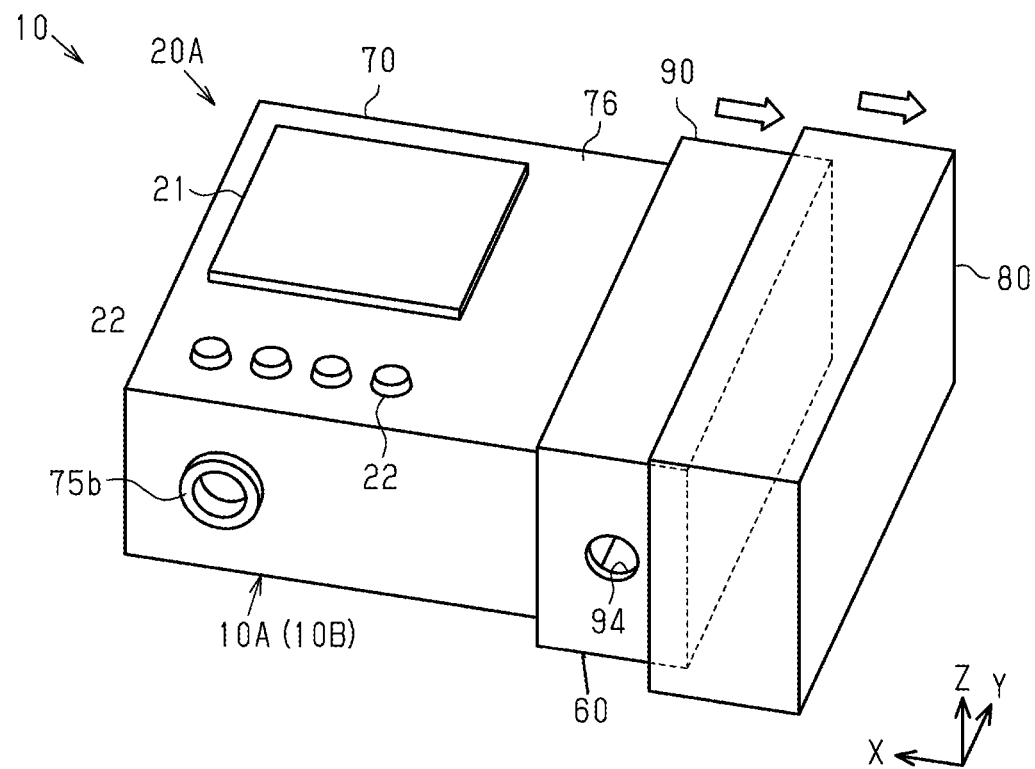
FIG. 8 is a perspective view of the air-blowing device that is in the second form in the fluid control apparatus according to the third embodiment.

As illustrated in FIG. 17A and FIG. 17B, the extension passage 140 includes a first wall 141 extending from the side wall 91 of the second partition-wall portion 90 in the transverse direction X, a second wall 142 extending from one of the side walls 75 of the first portion 70 toward the air-blowing chamber 72 in the transverse direction X, and the bottom wall 74 and the top wall 76 of the first portion 70 (see FIG. 8). The extension passage 140 is formed of the first wall 141, the second wall 142, the bottom wall 74 and the top wall 76 of the first portion 70, and the peripheral wall 92 of the second partition-wall portion 90.

With this configuration, the waves of the predominant sound that propagates through the extension passage 140 change to plane waves. As a result, the predominant sound in the suction path 28 is likely to be cancelled out by the first cavity 29a and the second cavity 29b of the silencer cavity 29.

Figure 18A:
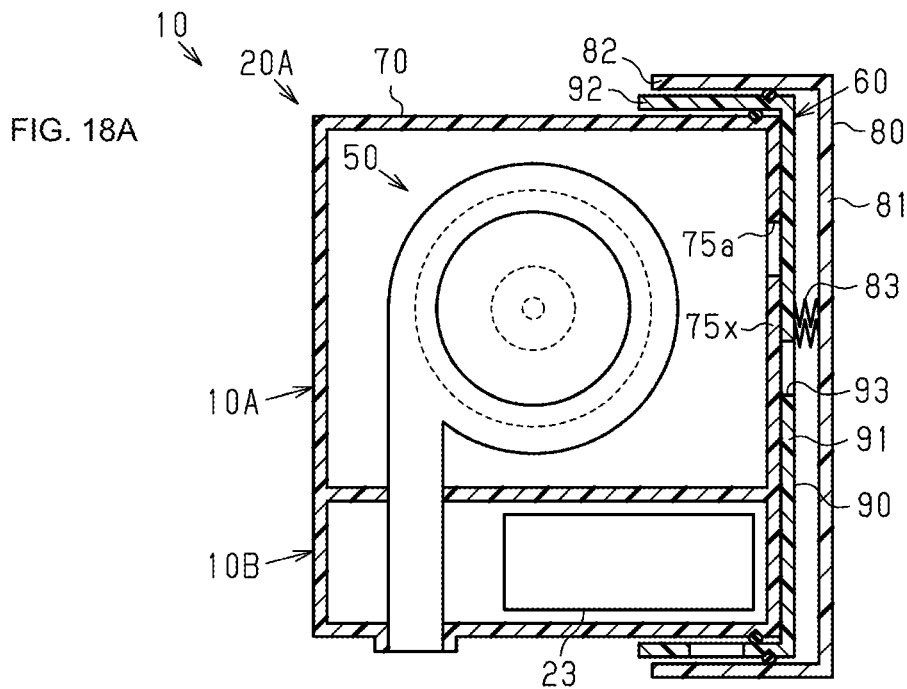
FIG. 18A is a plan sectional view of an air-blowing device in a fluid control apparatus according to another modification when the air-blowing device is in the first form.
Figure 18B:
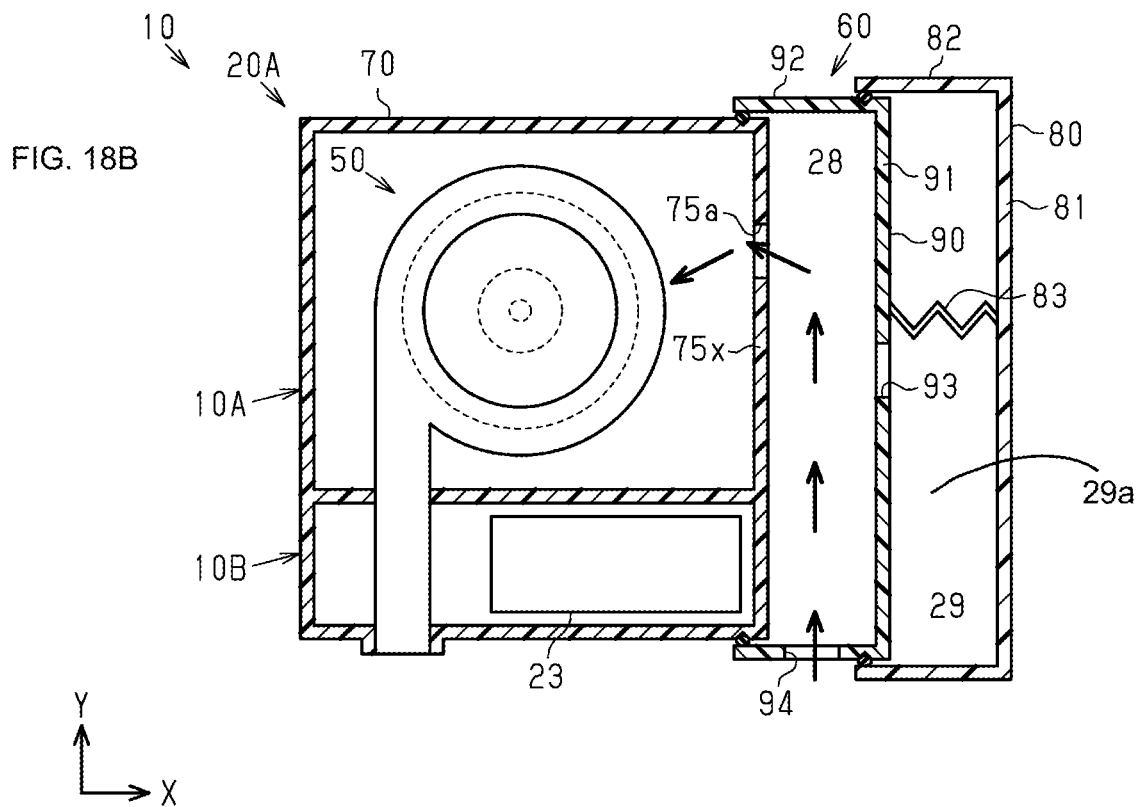
FIG. 18B is a plan sectional view of the air-blowing device in the fluid control apparatus according to this modification when the air-blowing device is in the second form.

In the fourth embodiment, the configuration of the partition unit 100 may be arbitrarily changed. For example, as illustrated in FIG. 18A and FIG. 18B, as a partition unit, a pleated expansion-and-contraction wall 83 that is connected to the side wall 91 of the second partition-wall portion 90 and the side wall 81 of the second portion 80 and that is capable of expanding and contracting in the transverse direction X may be employed. In the first form of the air-blowing device 10A illustrated in FIG. 18A, the expansion-and-contraction wall 83 contracts as a result of the second partition-wall portion 90 and the second portion 80 moving toward each other. In the second form of the air-blowing device 10A illustrated in FIG. 18B, the expansion-and-contraction wall 83 expands as a result of the second partition-wall portion 90 and the second portion 80 moving away from each other.

In the first to fourth embodiments, a silencer may be provided on an exhaust side of the air blower 50. Examples of the configuration of the silencer provided on the exhaust side of the air blower 50 include the following (B1) and (B2).

Figure 20A:
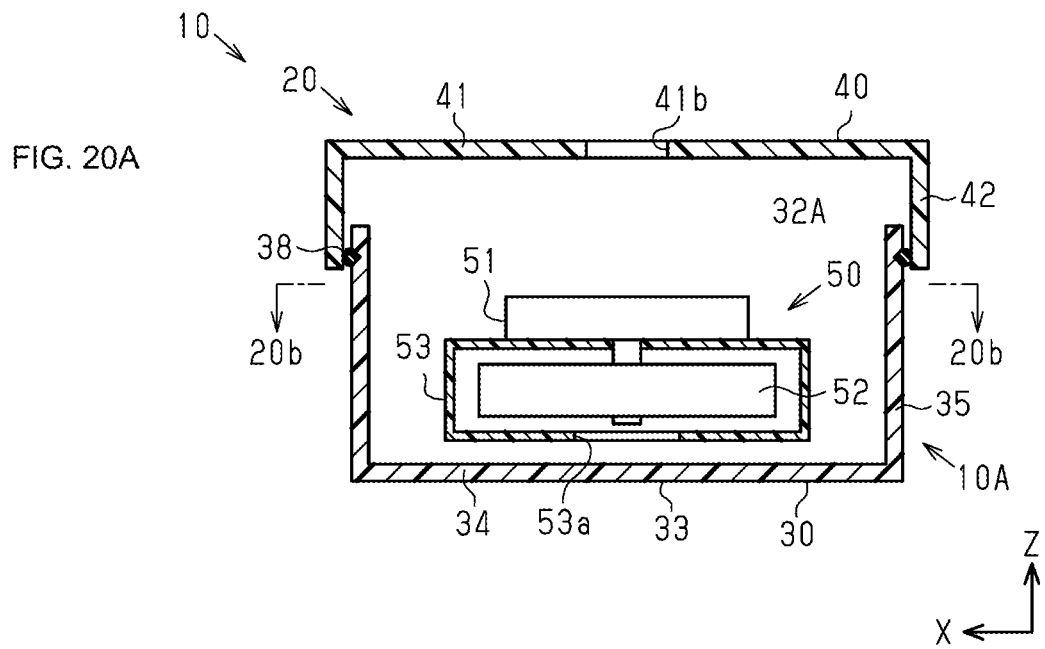
FIG. 20A is a sectional side view of the air-blowing device in the fluid control apparatus illustrated in FIG. 19B when the air-blowing device is in the second form.
Figure 20B:
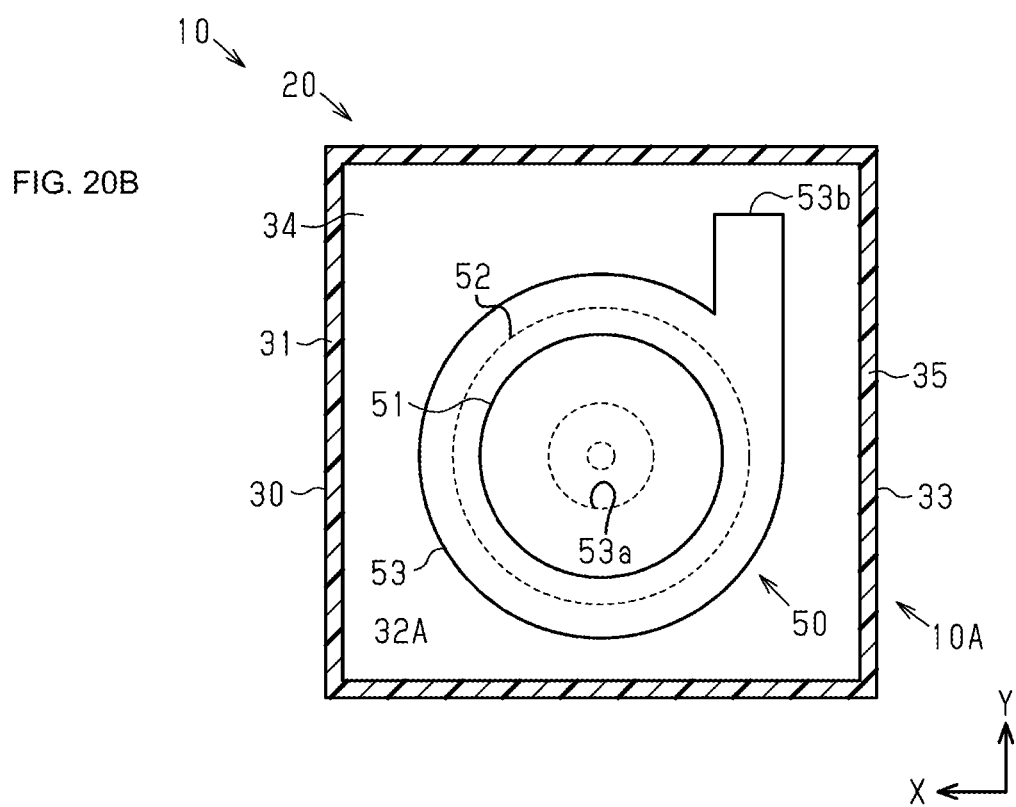
FIG. 20B is a plan sectional view of the air-blowing device in the fluid control apparatus illustrated in FIG. 19B when the air-blowing device is in the second form.

(B1) As illustrated in FIG. 19A and FIG. 19B, An intake hole 35d that is an example of the first cavity may be formed in the first side wall 35 of the first portion 33, and an exhaust hole 41b that is an example of the second cavity may be formed in the top wall 41 of the second portion 40. In the first form of the air-blowing device 10A illustrated in FIG. 19A, the side wall 42 of the second portion 40 covers the intake hole 35d of the first portion 33. In the second form of the air-blowing device 10A illustrated in FIG. 19B, the side wall 42 is moved to a position above the intake hole 35d, and thus, the intake hole 35d is exposed to the outside of the housing 20. In addition, as illustrated in FIG. 20B, the discharge port 53b of the air blower 50 is positioned further inside than the first side wall 35. As illustrated in FIG. 20A, in the second form of the air-blowing device 10A, an expandable silencer in which the volume of the air-blowing chamber 32A, which is in communication with the exhaust hole 41b, is increased to be larger than that in the first form is formed.

Figure 21A:
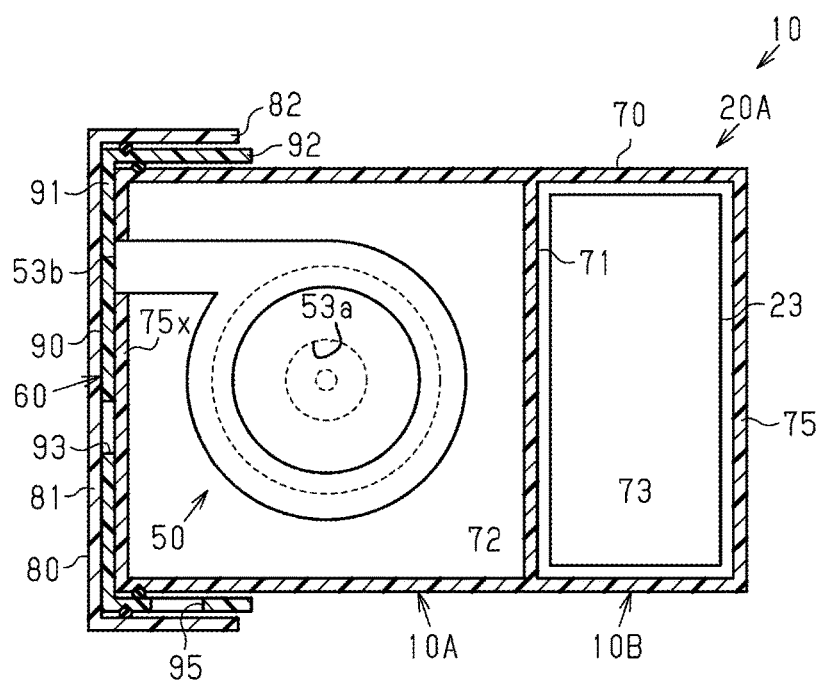
FIG. 21A is a plan sectional view of an air-blowing device in a fluid control apparatus according to another modification when the air-blowing device is in the first form.
Figure 21B:
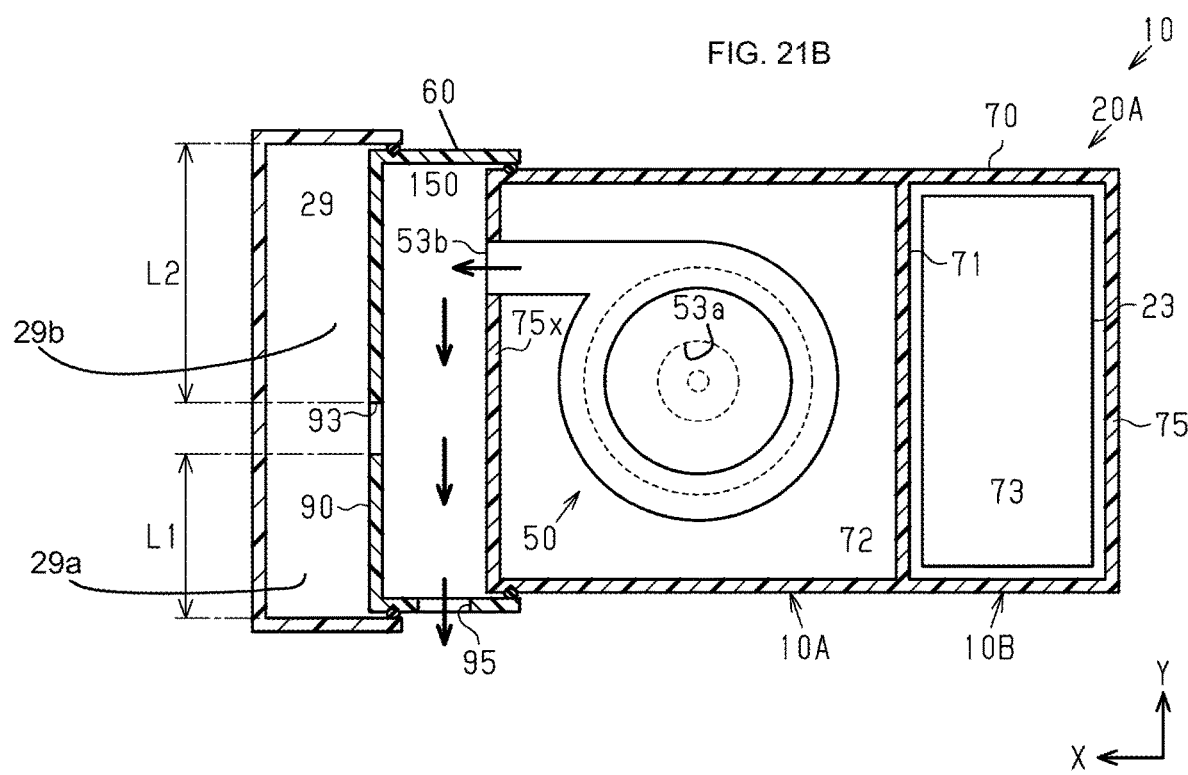
FIG. 21B is a plan sectional view of the air-blowing device in the fluid control apparatus according to this modification when the air-blowing device is in the second form.

(B2) As illustrated in FIG. 21B, a discharge path 150 may be formed between the first partition-wall portion 75x and the second partition-wall portion 90, and the silencer cavity 29 may be formed between the second partition-wall portion 90 and the second portion 80. As an example, the first partition-wall portion 75x is integrally formed with the first portion 70 so as to serve as one of the side walls of the first portion 70, the side wall being located on the side on which the second partition-wall portion 90 is present. The discharge path 150 allows the communication between the discharge port 53b of the air blower 50 and an exhaust hole 95 that is formed in the second partition-wall portion 90 and that is an example of the second cavity. The communication portion 93 allows the communication between the silencer cavity 29 and the discharge path 150. The silencer cavity 29 includes the first cavity 29a, which is a cavity positioned between the communication portion 93 and the exhaust hole 95 in the longitudinal direction of the silencer cavity 29, and the second cavity 29b, which is a cavity positioned between the communication portion 93 and the discharge port 53b in the longitudinal direction of the silencer cavity 29. As described above, in the second form of the air-blowing device 10A, a branched silencer is formed. Note that the position of the communication portion 93 can be arbitrarily set. As an example, as illustrated in FIG. 21B, the communication portion 93 is positioned closer to the exhaust hole 95 than the discharge port 53b is in the longitudinal direction Y. Thus, the length L1 of the first cavity 29a of the silencer cavity 29 is shorter than the length L2 of the second cavity 29b of the silencer cavity 29. Note that, in the air-blowing device 10A illustrated in FIG. 21A and FIG. 21B, an intake hole (not illustrated) that communicates with the air-blowing chamber 72 and that is an example of the first cavity is formed in the top wall 76 (see FIG. 8) of the first portion 70.

In the first form of the air-blowing device 10A illustrated in FIG. 21A, the second partition-wall portion 90 is accommodated in the space surrounded by the side wall 81 and the peripheral wall 82 of the second portion 80, and a portion of the first portion 70 in which the discharge port 53b is formed is accommodated in the space surrounded by the side wall 91 and the peripheral wall 92 of the second partition-wall portion 90. In FIG. 21A, the second partition-wall portion 90 and the portion of the first portion 70 in which the discharge port 53b is formed are accommodated in the space surrounded by the side wall 81 and the peripheral wall 82 of the second portion 80.

In the second form of the air-blowing device 10A illustrated in FIG. 21B, the discharge path 150 is formed as a result of one of the side walls 75 of the first portion 70 and the side wall 91 of the second partition-wall portion 90 moving away from each other, and the silencer cavity 29 is formed as a result of the side wall 91 of the second partition-wall portion 90 and the side wall 81 of the second portion 80 moving away from each other.

With this configuration, in the second form of the air-blowing device 10A, the discharge path 150 is formed outside the first portion 70, and thus, the silencer cavity 29, which communicates with the discharge path 150, is formed outside the first portion 70. Consequently, the silencer cavity 29 becomes a space dedicated to a silencer, and thus, the silencing effect is improved. Therefore, a decrease in the quietness of the air-blowing device 10A and the fluid control apparatus 1 when in use can be suppressed. In addition, in the first form of the air-blowing device 10A, that is, for example, when the patient P carries the air-blowing device 10A and the fluid control apparatus 1, the size of the housing 20A is reduced by reducing the volume of the discharge path 150, and thus, the portability of the air-blowing device 10A and the fluid control apparatus 1 when not in use can be improved.

In the first embodiment, the mounting structure of the first portion 33 and the second portion 40 may be arbitrarily changed. For example, the mounting structure of the first portion 33 and the second portion 40 may be changed as in the following (C1) and (C2). Similarly, the mounting structure of the first portion 70 and the second partition-wall portion 90 and the mounting structure of the second partition-wall portion 90 and the second portion 80 in the air-blowing device 10A of the second embodiment and in each of the air-blowing devices 10A of the third and fourth embodiments may also be changed.

(C1) As illustrated in FIG. 22A and FIG. 22B, the partition wall 31 and the first side wall 35 of the first portion 33 have a first recess 35e and a second recess 35f. The first recess 35e and the second recess 35f are each formed along the whole peripheries of the partition wall 31 and the first side wall 35. The first recess 35e and the second recess 35f are arranged so as to be spaced apart from each other in the heightwise direction Z. The side wall 42 of the second portion 40 includes a projection 42b that is capable of being fitted into the first recess 35e and the second recess 35f. The projection 42b is formed along the whole periphery of the side wall 42 at a lower end portion of the side wall 42. In the first form of the air-blowing device 10A illustrated in FIG. 22A, the projection 42b is fitted in the first recess 35e. In the second form of the air-blowing device 10A illustrated in FIG. 22B, the projection 42b is fitted in the second recess 35f. In this manner, in the first form and the second form of the air-blowing device 10A, as a result of the projection 42b fitting into one of the recesses 35e and 35f, the relative positions the first portion 33 and the second portion 40 in the heightwise direction Z can be maintained.

Figure 23:
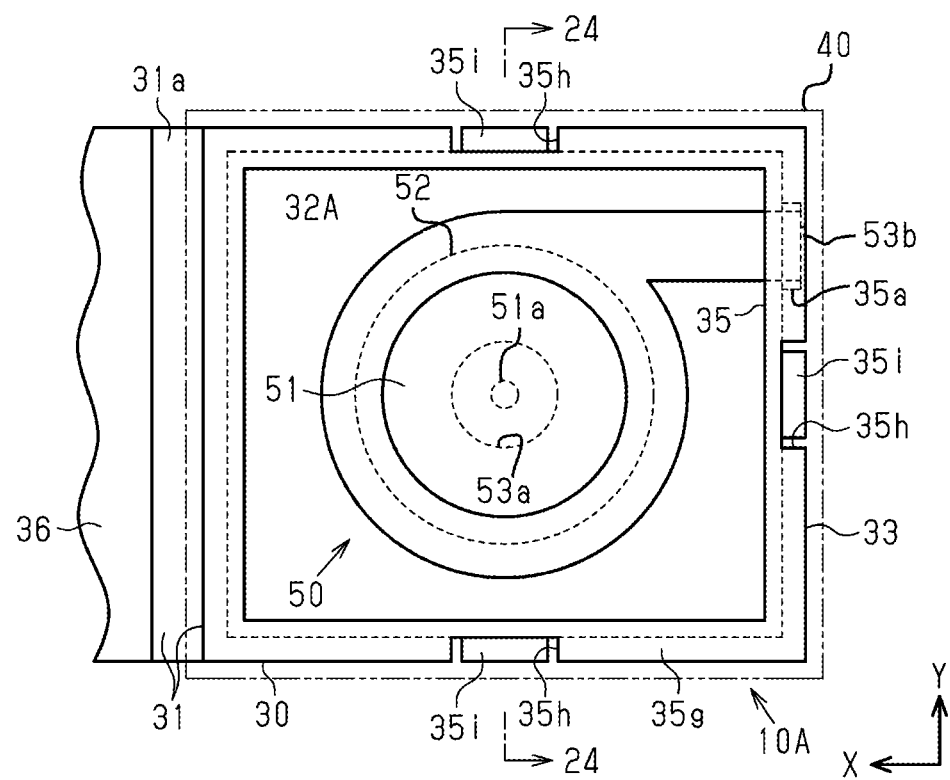
FIG. 23 is a plan view of a first portion of an air-blowing device in a fluid control apparatus according to another modification.
Figure 24A:
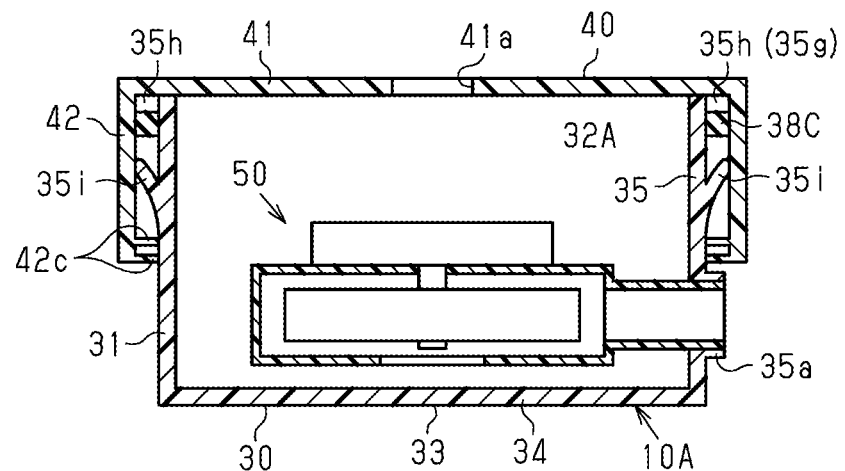
FIG. 24A is a sectional side view of the air-blowing device in the fluid control apparatus illustrated in FIG. 23 when the air-blowing device is in the first form.
Figure 24B:
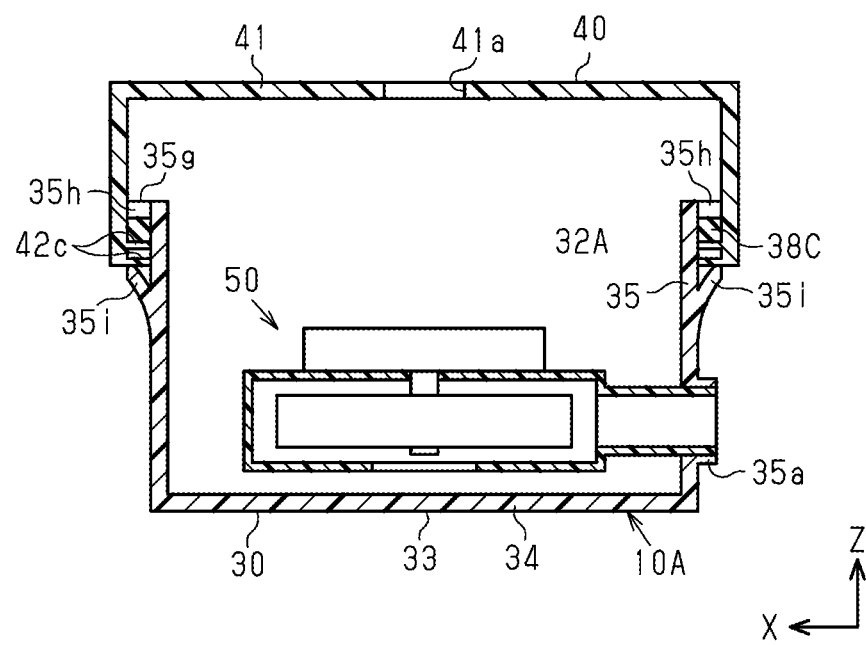
FIG. 24B is a sectional side view of the air-blowing device in the fluid control apparatus illustrated in FIG. 23 when the air-blowing device is in the second form.

(C2) As illustrated in FIG. 23, FIG. 24A, and FIG. 24B, the first portion 33 includes a flange portion 35g, a plurality of cutout portions 35h that are formed in the flange portion 35g, and a plurality of hook portions 35i that are provided at positions corresponding to the cutout portions 35h. In addition, an elastic member 38C that has an annular shape is attached to the first portion 33 so as to be in contact with the bottom surface of the flange portion 35g and the outer surface of the first side wall 35. Note that the elastic member 38C is not illustrated in FIG. 23 for convenience of description. The hook portions 35i are located lower than the elastic member 38C. As illustrated in FIG. 24A and FIG. 24B, the side wall 42 of the second portion 40 includes a pair of protruding portions 42c that is to be sandwiched between the elastic member 38C and the hook portions 35i. The pair of protruding portions 42c is formed along the whole periphery of the side wall 42 at the lower end portion of the side wall 42. In the first form of the air-blowing device 10A illustrated in FIG. 24A, the pair of protruding portions 42c are located lower than the upper end portions of the hook portions 35i. In the second form of the air-blowing device 10A illustrated in FIG. 24B, the pair of protruding portions 42c are sandwiched between the hook portions 35i and the elastic member 38C. In this case, the pair of protruding portions 42c is pressed toward the elastic member 38C by the hook portions 35i. As a result, the sealing performance of the pair of protruding portions 42c and the elastic member 38C is improved. Consequently, the probability of the air leaking from a gap between the first side wall 35 of the first portion 33 and the side wall 42 of the second portion 40 is reduced, and thus, a decrease in the flow-rate characteristics of the air-blowing device 10A can be suppressed.

In the second embodiment, although the partition-wall portion 60 is integrally formed with the first portion 33, the configuration of the partition-wall portion 60 is not limited to this and may be arbitrarily changed. For example, the partition-wall portion 60 may be integrally formed with the second portion 40. Alternatively, the partition-wall portion 60 may be formed separately from the first portion 33 and the second portion 40. In other words, the partition-wall portion 60 may at least be configured to be capable of isolating the space inside the first portion 33 and the space inside the second portion 40 from each other.

In the fifth embodiment, the configuration of the movable unit 114 of the silencer 110 may be arbitrarily changed. For example, the silencer 110 includes the cylindrical first connecting portion 112 and the cylindrical second connecting portion 113 in which the first connecting portion 112 is accommodated. Instead of a pleated movable unit, for example, the movable unit may have a configuration for enabling the first connecting portion 112 and the second connecting portion 113 to move relative to each other like the sliding structure of the movable unit 25 that enables the first portion 33 and the second portion 40 of the housing 20 of the first embodiment to move relative to each other.

In the fifth embodiment, the air-blowing device 10A may include one of the housings 20 and 20A of the first to fourth embodiments instead of the housing 20B.

In each of the embodiments, the first portion 33 may form a part of the case 53 of the air blower 50.

In the third and fourth embodiments, the position of the outer intake hole 94 may be arbitrarily changed. For example, as illustrated in FIG. 25A, the outer intake hole 94 may be formed in the peripheral wall 82 of the second portion 80. In this case, as illustrated in FIG. 25B, the suction path 28 is formed between the second partition-wall portion 90 and the second portion 80. An intermediate intake hole 96 is formed in a portion of the second partition-wall portion 90, the portion facing the inner intake hole 75a. In the suction path 28, the passage 28a that has a constant passage cross-sectional area is formed between the intermediate intake hole 96 and the communication portion 93. The passage 28a is a passage extending from the intermediate intake hole 96 to the communication portion 93 in the suction path 28. The partition wall 97 that is capable of being inserted into the inner intake hole 75a is formed in the vicinity of the intermediate intake hole 96 so as to be integral with the second partition-wall portion 90. When the air-blowing device 10A is in the first form illustrated in FIG. 25A, the partition wall 97 is located in the air-blowing chamber 72, and when the air-blowing device 10A is in the second form illustrated in FIG. 25B, the partition wall 97 partitions the space between one of the side walls 75 of the first portion 70 and the second partition-wall portion 90. Thus, the silencer cavity 29 is formed as the space surrounded by the side wall 75 of the first portion 70, the second partition-wall portion 90, and the partition wall 97. The silencer cavity 29 includes the first cavity 29a, which is a space located on the side on which the outer intake hole 94 is present with respect to the communication portion 93, and the second cavity 29b, which is a space located on the side on which the partition wall 97 is present with respect to the communication portion 93. With this configuration, advantageous effects similar to those of the third embodiment can be obtained. Note that the length L1 of the first cavity 29a and the length L2 of the second cavity 29b may be arbitrarily changed in accordance with the noise of the frequency to be reduced. In the fourth embodiment, in the case where the outer intake hole 94 is formed in the peripheral wall 82 of the second portion 80, the partition unit 100 is provided between the first partition-wall portion 75x and the second partition-wall portion 90.

In the air-blowing device 10A illustrated in FIGS. 21A and 21B, the position of the exhaust hole 95 may be arbitrarily changed. For example, as illustrated in FIG. 26A, the exhaust hole 95 may be formed in the peripheral wall 82 of the second portion 80. In this case, as illustrated in FIG. 26B, the discharge path 150 is formed between the second partition-wall portion 90 and the second portion 80. An inner exhaust hole 98 is formed in a portion of the second partition-wall portion 90, the portion facing the discharge port 53b. A partition wall 99 that is capable of being inserted into one of the side walls 75 of the first portion 70, the side wall 75 being located on the side on which the second partition-wall portion 90 is present, is formed in the vicinity of the inner exhaust hole 98 so as to be integral with the second partition-wall portion 90. When the air-blowing device 10A is in the first form illustrated in FIG. 26A, the partition wall 99 is located in the air-blowing chamber 72, and when the air-blowing device 10A is in the second form illustrated in FIG. 26B, the partition wall 99 partitions the space between the side wall 75 of the first portion 70 and the second partition-wall portion 90. Thus, the silencer cavity 29 is formed as the space surrounded by the side wall 75 of the first portion 70, the second partition-wall portion 90, and the partition wall 99. The silencer cavity 29 includes the first cavity 29a, which is a space between the communication portion 93 and the exhaust hole 95, and the second cavity 29b, which is a space between the communication portion 93 and the partition wall 99. Note that the length L1 of the first cavity 29a and the length L2 of the second cavity 29b may be arbitrarily changed in accordance with the noise of the frequency to be reduced.

In the third and fourth embodiments, a Helmholtz silencer may be employed. More specifically, the passage cross-sectional area of a portion that extends from the communication portion 93 to the silencer cavity 29 (an entry portion in the silencer cavity 29 that is in communication with the suction path 28) is set to be sufficiently smaller than the passage cross-sectional area of the rest of the silencer cavity 29. As a result, advantageous effects similar to those of the third embodiment can be obtained.

In the third and fourth embodiments, the control device 10B may be capable of changing the rotational speed of the air blower 50 (the rotational speed of the motor 51) to any one of a plurality of speed levels. In addition, in the air-blowing device 10A, the volume of the housing 20A may be changed to any one of a plurality of volume levels. More specifically, in the air-blowing device 10A, the volume of the silencer cavity 29, which is surrounded by the second partition-wall portion 90 and the second portion 80, may be changed to any one of a plurality of volume levels. As an example, the set level of the rotational speed of the air blower 50 and the set level of the volume of the silencer cavity 29 are associated with each other. In this case, the rotational speed of the air blower 50 is set to avoid a frequency at which the transmission loss becomes zero in the frequency characteristics of the transmission loss that is determined by the volume of the silencer cavity 29. Preferably, the rotational speed of the air blower 50 is set to a frequency at which the transmission loss becomes maximum in the frequency characteristics of the transmission loss that is determined by the volume of the silencer cavity 29.

With this configuration, by changing the internal volume of the housing 20A, the frequency at which the transmission loss based on the rotational speed of the air blower 50 becomes zero can be avoided. Therefore, a decrease in the quietness of the air-blowing device 10A when in use can be suppressed.

In the first to fourth embodiments, each of the movable units 25, 27A, and 27B of the air-blowing device 10A may include a motor serving as a driving source and a rotational-to-linear motion conversion mechanism that changes the rotational motion of the output shaft of the motor to linear motion. Each of movable units 25, 27A, and 27B changes between the first form and the second form based on the operation of the operation unit 22. As an example, when an operation for switching on the fluid control apparatus 1 or an operation for driving the air blower 50 is performed by operating the operation unit 22, each of movable units 25, 27A, and 27B changes from the first form to the second form. The increased amount in the internal volume of each of the housings 20 and 20A in the second form may be changed by the motor in accordance with the patient P. As an example, the increased amount in the internal volume of each of the housings 20 and 20A in the second form is changed in accordance with the rotational speed of the air blower 50. As a result, noise can be reduced in accordance with noise characteristics at the rotational speed of the air blower 50 that is suitable for the patient P.

In each of the embodiments, the air-blowing device 10A may further include an indicating unit that indicates the form of the air-blowing device 10A to the patient P. An example of the indicating unit is a light-emitting unit that is provided in or on the housing 20 (20A, 20B). When the air-blowing device 10A is in the second form, the light-emitting unit emits light. An example of the light-emitting unit is a light-emitting diode (LED).

In each of the embodiments, the air-blowing device 10A and the control device 10B may be individually formed. In this case, the air-blowing device 10A and the control device 10B may be configured so as to be separated from each other. The air-blowing device 10A and the control device 10B that are separated from each other may be electrically connected to each other by a wired connection such as a harness or by a wireless connection such as radio waves.

1 fluid control apparatus
10A air-blowing device
11 tube
12 mask
20, 20A, 20B housing
25, 114, 120, 130 movable unit
27A first movable unit (movable unit)
27B second movable unit (movable unit)
28 suction path
33, 70 first portion
35a exhaust portion (second cavity)
39x intake hole (first cavity)
40, 80 second portion
35d, 41a intake hole (first cavity)
41b exhaust hole (second cavity)
50 air blower
53a suction port
53b discharge port
60 partition-wall portion
61, 93 communication portion
75b exhaust hole (second cavity)
75x first partition-wall portion
90 second partition-wall portion
94 outer intake hole (first cavity)
95 exhaust hole (second cavity)
100 partition unit
110 silencer
150 discharge path

The invention claimed is:

1. An air-blowing device comprising:
an air blower; and
a housing including a first cavity and a second cavity and accommodating the air blower, wherein a fluid flows into the first cavity and is discharged from the second cavity when the air blower is driven,
wherein the housing is expandable and contractible so as to change an internal volume of the housing, wherein the housing includes a first portion and a second portion, the first portion defining a first space with said air blower therein, the second portion being configured to move relative to the first portion between a first form and a second form, wherein the second portion covers a part of the first portion and defines a second space when the second portion is moved to the second form, and wherein the first portion includes a partition-wall portion partitioning the second space and the first space from each other.

2. The air-blowing device according to claim 1,
wherein the housing is expandable and contractible so as to change a volume of an internal space surrounded by the first portion and the second portion.

3. The air-blowing device according to claim 1,
wherein the housing includes a movable unit causing the first portion and the second portion to move relative to each other.

4. The air-blowing device according to claim 1,
wherein the partition-wall portion has a communication portion allowing communication between the first space inside the first portion and the second space inside the second portion.

5. The air-blowing device according to claim 4,
wherein the second portion includes the first cavity or the second cavity, and
wherein an opening surface of the communication portion located on a side of the second portion faces an opening surface of the first cavity or the second cavity included in the second portion.

6. The air-blowing device according to claim 4, further comprising:
a suction path allowing communication between the first cavity and a suction port of the air blower,
wherein the partition-wall portion includes a first partition-wall portion and a second partition-wall portion,
wherein the first partition-wall portion is disposed between the first portion and the second partition-wall portion,
wherein the second partition-wall portion is disposed between the first partition-wall portion and the second portion,
wherein the first portion includes the second cavity, and
wherein the suction path is provided between the first partition-wall portion and the second partition-wall portion or between the second partition-wall portion and the second portion.

7. The air-blowing device according to claim 4, further comprising:
a discharge path allowing communication between the second cavity and a discharge port of the air blower,
wherein the partition-wall portion includes a first partition-wall portion and a second partition-wall portion,
wherein the first partition-wall portion is disposed between the first portion and the second partition-wall portion,
wherein the second partition-wall portion is disposed between the first partition-wall portion and the second portion,
wherein the first portion includes the first cavity, and
wherein the discharge path is provided between the first partition-wall portion and the second partition-wall portion or between the second partition-wall portion and the second portion.

8. The air-blowing device according to claim 6,
wherein the second partition-wall portion is attached to the first portion so as to be movable relative to the first portion.

9. The air-blowing device according to claim 8,
wherein the second portion is attached to the second partition-wall portion so as to be movable relative to the second partition-wall portion, and
wherein a direction of movement of the second partition-wall portion with respect to the first portion and a direction of movement of the second portion with respect to the second partition-wall portion are the same direction.

10. The air-blowing device according to claim 6,
wherein the second portion includes a partition unit partitioning an internal space provided by the second partition-wall portion and the second portion.

11. The air-blowing device according to claim 3,
wherein the movable unit connects the first portion and the second portion to each other so as to hermetically seal an internal space between the first portion and the second portion and is expandable and contractible in a direction in which the first portion and the second portion move relative to each other.

12. The air-blowing device according to claim 3,
wherein the movable unit causes the first portion and the second portion to move relative to each other between the first form and the second form, wherein in the first form, the first portion is accommodated in the second portion and in the second form, the first portion accommodated projects from the second portion.

13. The air-blowing device according to claim 1,
wherein the housing further includes a silencer detachably attached to the first cavity or the second cavity, and
wherein the silencer is expandable and contractible so as to change an internal volume of the silencer.

14. The air-blowing device according to claim 1,
wherein a rotational speed of the air blower is settable to any one of a plurality of speed levels, and
wherein the internal volume of the housing is changeable to any one of a plurality of volume levels.

15. A fluid control apparatus comprising:
the air-blowing device according to claim 1; and
a tube connecting the second cavity of the air-blowing device to a mask or a nasal cannula and supplying a gas from the second cavity to the mask or the nasal cannula.

16. The air-blowing device according to claim 3,
wherein the partition-wall portion has a communication portion allowing communication between the first space inside the first portion and the second space inside the second portion.

17. The air-blowing device according to claim 7,
wherein the second partition-wall portion is attached to the first portion so as to be movable relative to the first portion.

18. The air-blowing device according to claim 7,
wherein the second portion includes a partition unit partitioning an internal space provided by the second partition-wall portion and the second portion.

19. The air-blowing device according to claim 8,
wherein the second portion includes a partition unit partitioning an internal space provided by the second partition-wall portion and the second portion.

20. The air-blowing device according to claim 9,
wherein the second portion includes a partition unit partitioning an internal space provided by the second partition-wall portion and the second portion.

* * * * *